(12) United States Patent
Rhee et al.

(10) Patent No.: US 11,568,758 B2
(45) Date of Patent: Jan. 31, 2023

(54) TERMINAL

(71) Applicant: LG ELECTRONICS INC., Seoul (KR)

(72) Inventors: Eunjoo Rhee, Seoul (KR); Choil Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 323 days.

(21) Appl. No.: 16/634,561

(22) PCT Filed: Mar. 23, 2018

(86) PCT No.: PCT/KR2018/003428
§ 371 (c)(1),
(2) Date: Jan. 27, 2020

(87) PCT Pub. No.: WO2019/022337
PCT Pub. Date: Jan. 31, 2019

(65) Prior Publication Data
US 2020/0265741 A1  Aug. 20, 2020

(30) Foreign Application Priority Data

Jul. 27, 2017  (KR) .................. 10-2017-0095570

(51) Int. Cl.
*G09B 19/00* (2006.01)
*G06F 16/22* (2019.01)
(Continued)

(52) U.S. Cl.
CPC ................ *G09B 19/00* (2013.01); *A61B 5/18* (2013.01); *A61B 5/7264* (2013.01);
(Continued)

(58) Field of Classification Search
CPC ......... G09B 19/00; G09B 19/19; G06F 16/22; G06N 20/00; H04M 1/72454; A61B 5/18;
(Continued)

(56) References Cited

U.S. PATENT DOCUMENTS

2018/0150749 A1* 5/2018 Wu .................... G06Q 30/0269
2020/0265741 A1* 8/2020 Rhee .................... G06F 16/337

FOREIGN PATENT DOCUMENTS

JP  2003014474  1/2003
JP  2017117360  6/2017
(Continued)

OTHER PUBLICATIONS

PCT International Application No. PCT/KR2018/003428, International Searching Authority dated Jun. 28, 2018, 4 pages.

*Primary Examiner* — Khai M Nguyen
(74) *Attorney, Agent, or Firm* — Lee Hong Degerman Kang Waimey

(57) ABSTRACT

A terminal is disclosed. The terminal according to an embodiment of the present invention comprises: an output unit for outputting a notification; a storage unit for storing a database; a control unit for controlling the outputting of the notification; and an artificial intelligence unit for acquiring information regarding a user's context, and outputting a notification when the user's context corresponds to information included in the database, wherein the database includes at least one of a user's personal database, a standard activity database, and an accident type database.

13 Claims, 13 Drawing Sheets

(51) Int. Cl.
   *G06N 20/00*     (2019.01)
   *A61B 5/18*      (2006.01)
   *A61B 5/00*      (2006.01)
   *G01C 21/34*     (2006.01)
   *G06Q 30/06*     (2012.01)
   *H04M 1/72454*   (2021.01)
   *G09B 19/14*     (2006.01)

(52) U.S. Cl.
   CPC ..... *G01C 21/3484* (2013.01); *G01C 21/3492* (2013.01); *G06F 16/22* (2019.01); *G06N 20/00* (2019.01); *G06Q 30/0631* (2013.01); *H04M 1/72454* (2021.01); *G09B 19/14* (2013.01)

(58) Field of Classification Search
   CPC .............. A61B 5/7264; G01C 21/3484; G01C 21/3492; G06Q 30/0631
   See application file for complete search history.

(56) References Cited

FOREIGN PATENT DOCUMENTS

| | | | | |
|---|---|---|---|---|
| KR | 20140048424 | | 4/2014 | |
| KR | 20150086909 | | 7/2015 | |
| KR | 20150086909 | A * | 7/2015 | |
| KR | 20150086909 | A * | 8/2015 | |
| KR | 20060106425 | | 10/2016 | |
| WO | WO-2019240062 | A1 * | 12/2019 | ............ H04M 19/04 |

* cited by examiner

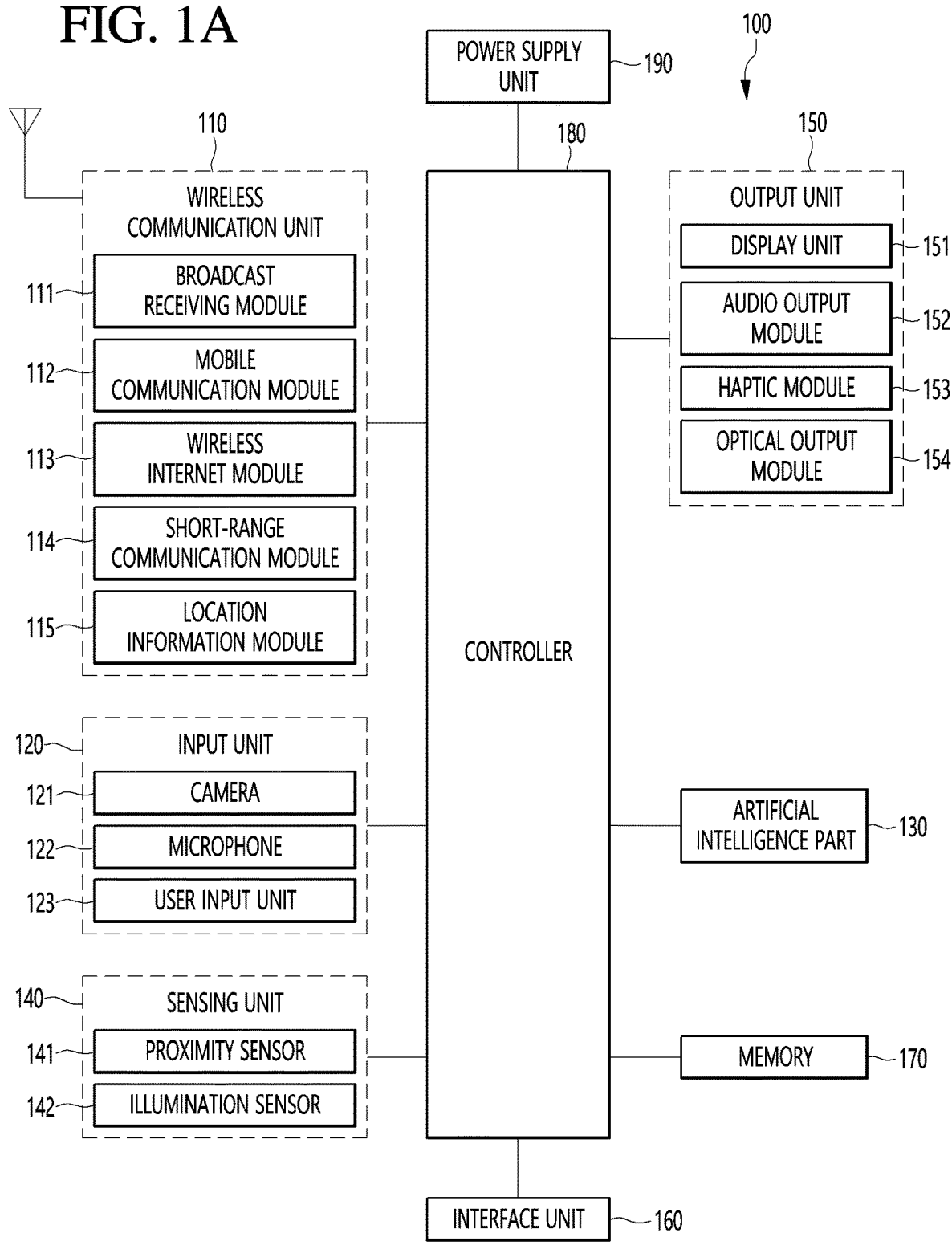

FIG. 9
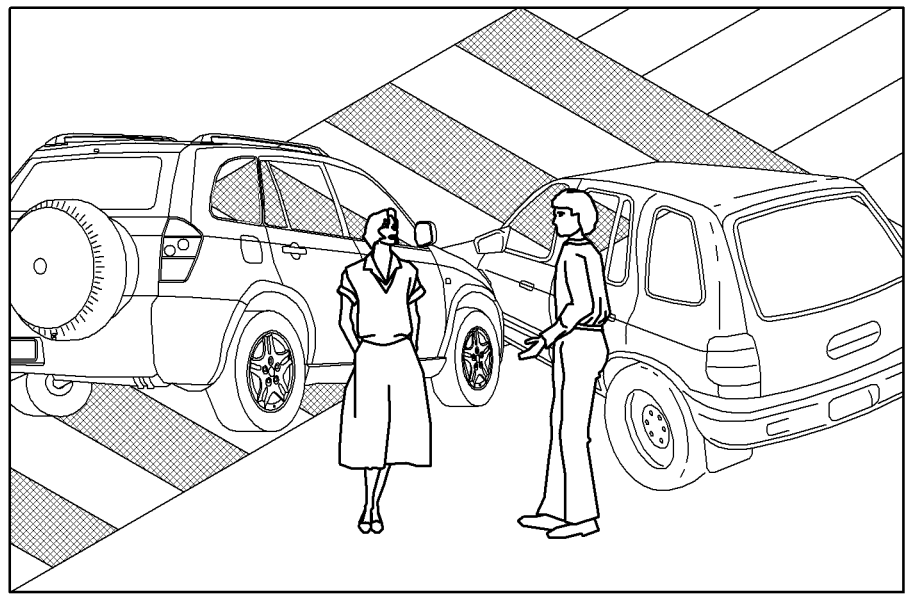
(a)
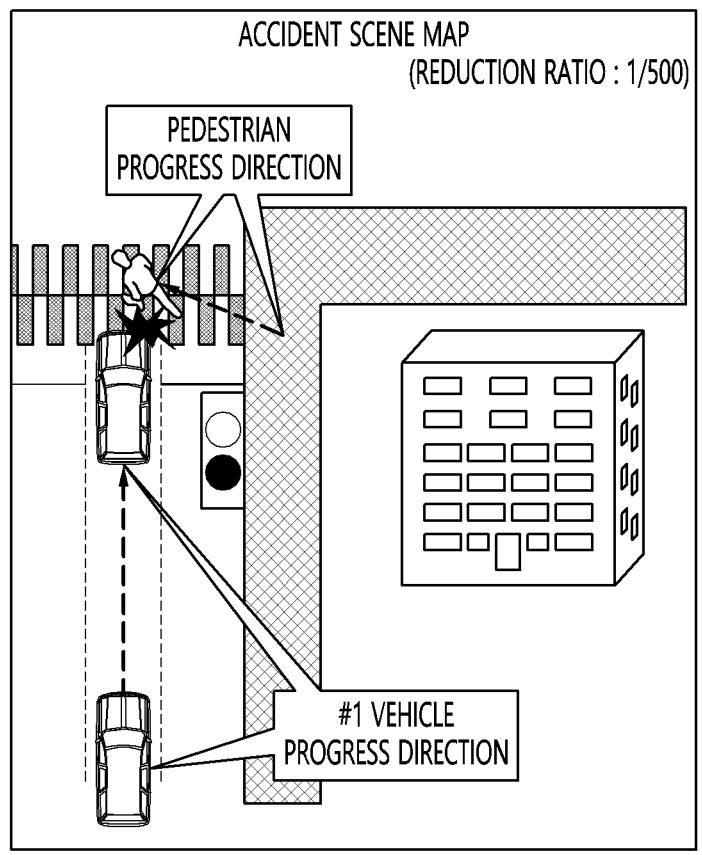
(b)

FIG. 14
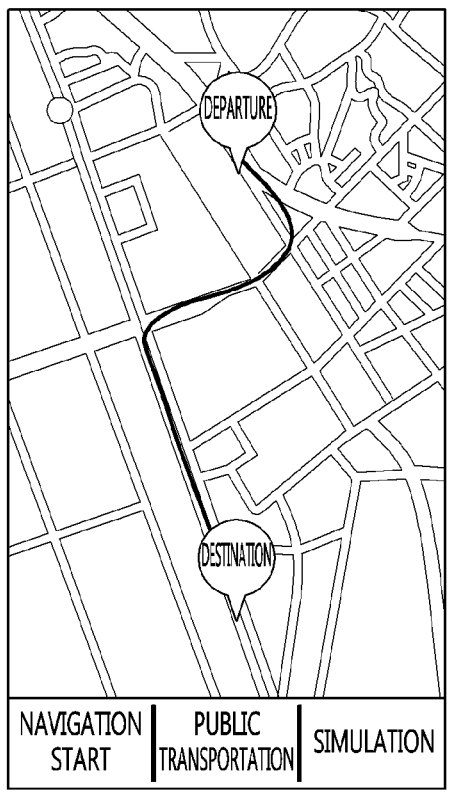
(a)
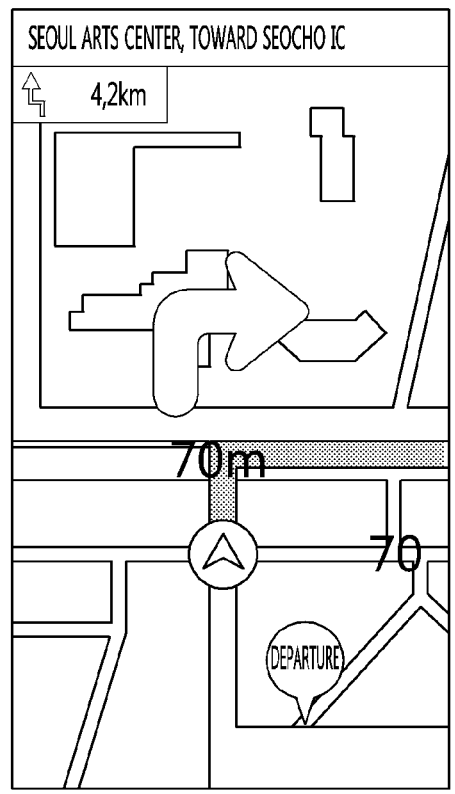
(b)

TERMINAL

CROSS-REFERENCE TO RELATED APPLICATIONS

This application is the National Stage filing under 35 U.S.C. 371 of International Application No. PCT/KR2018/003428, filed on Mar. 23, 2018, which claims the benefit of earlier filing date and right of priority to Korean Application No. 10-2017-0095570, filed on Jul. 27, 2017, the contents of which are all incorporated by reference herein in their entirety.

TECHNICAL FIELD

The present disclosure relates to a terminal capable of providing a guide to a user's behavior using various databases.

BACKGROUND ART

Artificial intelligence refers to one field of computer engineering and information technology of studying a method for making a computer think, learn, and do self-improvement, which is achieved based on human intelligence, and means that a computer emulates an intelligent behavior of the human.

AI is largely related directly and indirectly to other fields of a computer science rather than existing itself. In particular, AI elements have been modernly introduced in various fields of information technology, and there has been an active attempt to use AI to overcome problems of the fields.

Research has been actively conducted into context awareness technology of recognizing a situation of a user and providing information desired by the user in a desired form using conventional AI.

The aforementioned context awareness technology has been developed, and simultaneously, demands for mobile terminals for performing functions suitable for a situation of a user have increased.

Meanwhile, it is necessary for a user to know user's past behaviors or habits of repeating certain behaviors. However, the user may not remember them or may not even recognize their habits.

Therefore, there is an increasing need for reminding a user of user's behaviors or habits using a context awareness function of artificial intelligence.

DISCLOSURE

Technical Problem

An object of the present disclosure devised to solve the problem lies in a terminal capable of providing a guide to a user's behavior using various databases.

Technical Solution

A terminal according to an embodiment may include an output interface configured to output a notification, a memory configured to store a database, a controller configured to control output of the notification, and an artificial intelligence interface configured to acquire information on a situation of a user and output a notification when the situation of the user corresponds to information included in the database. The database includes at least one of a personal database of the user, a standard behavior database or an accident type database.

In this case, the standard behavior database may include information on a behavior of a driver while driving, and the artificial intelligence interface may acquire information on a behavior of the user and outputs the notification when the behavior of the user corresponds to the behavior of the driver included in the standard behavior database.

In this case, the standard behavior database may include information on a position and information on a behavior of a driver at the position, and the artificial intelligence interface may output the notification when the user passes the position and the behavior of the user corresponds to the behavior of the driver at the position.

The standard behavior database may include information on an incorrect behavior of a driver while driving, the memory may include information on a correct behavior corresponding to the incorrect behavior, and the artificial intelligence interface may output the correct behavior when the behavior of the user corresponds to the incorrect behavior.

The personal database of the user may include information on a behavior pattern acquired from a past behavior of the user, and the artificial intelligence interface may acquire information on the behavior of the user and determine whether the notification is output or an intensity of the notification based on whether the behavior of the user corresponds to the behavior pattern.

The artificial intelligence interface may acquire and store a behavior pattern of a user corresponding to the standard behavior database based on a behavior of the user and the standard behavior database, and output the notification when the behavior of the user corresponds to the behavior pattern.

The accident type database may include information on a position and information on an accident type at the position, and the artificial intelligence interface may output a notification corresponding to the accident type at the position when the user passes the position.

In this case, the artificial intelligence interface may acquire information on a driving state of the user, and output a notification corresponding to the accident type based on the driving state of the user and the accident type when the user passes the position.

The artificial intelligence interface may acquire a driving habit including at least one of information on a traffic regulation violation of the user or information on route deviation of the user, store the driving habit and position information corresponding to the driving habit in the personal database, and output a notification related to the driving habit at a position where the driving habit appears.

In this case, the artificial intelligence interface may output a notification for preventing the traffic regulation violation when the user reaches a position where the traffic regulation violation appears, based on the information on the traffic regulation violation and position information corresponding to the traffic regulation violation.

The artificial intelligence interface may output a notification for preventing the route deviation when the user reaches a position where the route deviation appears, based on the information on the route deviation and position information corresponding to the information on the route deviation.

The artificial intelligence interface may acquire information on a movement route to be used by the user based on a past movement route of the user and current movement of the user and provide a guide to a new route based on route information of the movement route to be used by the user, and the route information may include at least one of a traffic condition of the route or a route faster than a route used by the user in the past.

The personal database may include a consumption list of the user, and the artificial intelligence interface may acquire a consumption pattern of the user based on the consumption list of the user, and output a notification indicating a consumption state of the user based on the consumption pattern and the consumption list.

The personal database may include a list of items of the user, and the artificial intelligence interface may acquire information on an item, which needs to be purchased, based on at least one of a purchase time, a purchase frequency or a distribution period of an item included in the list of items, and output a notification for purchasing the item in the vicinity of a place where the item, which needs to be purchased, is capable of being acquired.

The standard behavior database may include information on a person's life pattern, and the artificial intelligence interface may acquire information on a life pattern of the user, and output a warning notification based on information on the life pattern of the user and information on the person's life pattern.

DESCRIPTION OF DRAWINGS

FIG. 1A is a block diagram illustrating a mobile terminal according to the present disclosure.

FIGS. 8 to 9 are views illustrating a method of outputting a notification based on an accident type database according to an embodiment of the present disclosure.

FIGS. 12 to 15 are views illustrating a method of guiding a route based on a route pattern of a user according to an embodiment of the present disclosure.

BEST MODE

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1B:
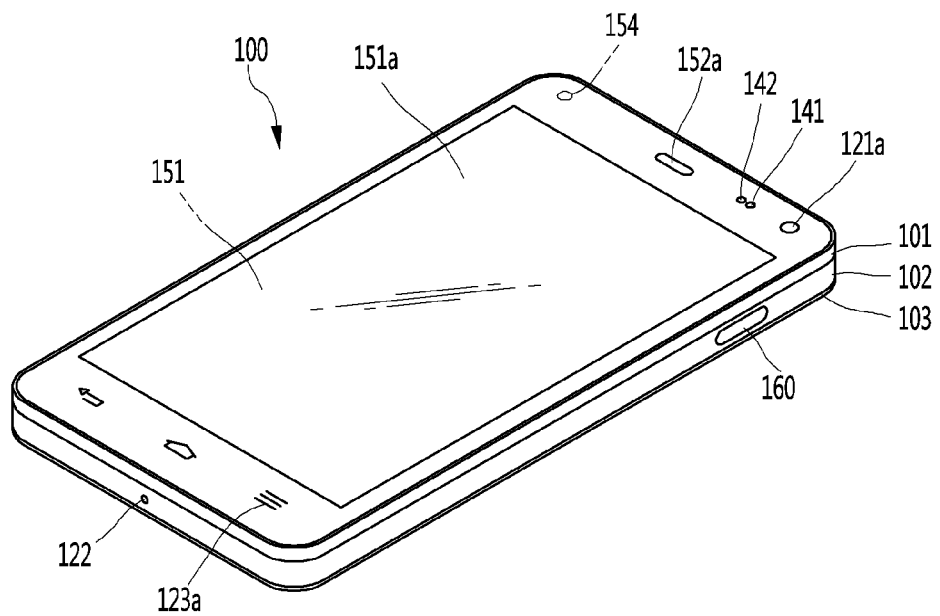
FIGS. 1b and 1c are conceptual views showing an examples of a mobile terminal according to the present disclosure when viewed from different directions.
Figure 1C:
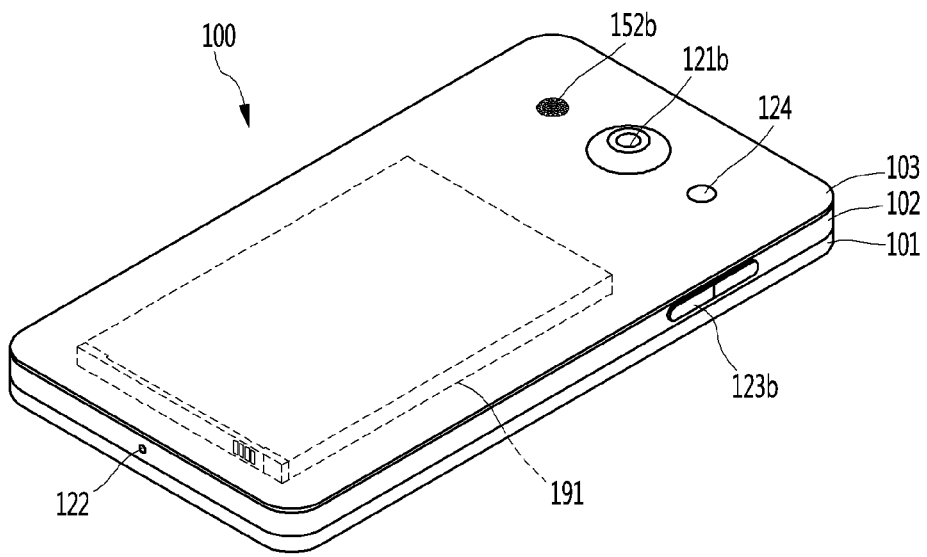

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions.

The mobile terminal 100 is shown having components such as a wireless communication unit 110, an input interface 120, a sensing unit 140, an output interface 150, an interface 160, a memory 170, a controller 180, and a power supply unit 190. It is understood that implementing all of the illustrated components is not a requirement, and that greater or fewer components may alternatively be implemented.

Referring now to FIG. 1A, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

To facilitate such communications, the wireless communication unit 110 includes one or more of a broadcast receiving module 111, a mobile communication module 112, a wireless Internet module 113, a short-range communication module 114, and a location information module 115.

The input interface 120 includes a camera 121 for obtaining images or video, a microphone 122, which is one type of audio input device for inputting an audio signal, and a user input interface 123 (for example, a touch key, a push key, a mechanical key, a soft key, and the like) for allowing a user to input information. Data (for example, audio, video, image, and the like) is obtained by the input interface 120 and may be analyzed and processed by controller 180 according to device parameters, user commands, and combinations thereof.

An artificial intelligence part 130 may process information based on artificial intelligence technology and may include one or more modules for performing at least one of information learning, information inference, information perception, or natural language processing.

The artificial intelligence part 130 may perform at least one of learning, inference, or processing on a massive amount of information (big data) such as information stored in a mobile terminal, information on an environment around the mobile terminal, or information stored in an external memory that is capable of communicating, using machine learning technology. The artificial intelligence part 130 may predict (or infer) at least one executable operation of a mobile terminal using learned information using the machine learning technology, and may control the mobile terminal to perform an operation with the highest realistic possibility among the at least one predicted operations.

The machine learning technology is technology of collecting and learning a massive amount of information and determining and predicting information based on the learned information, using at least one algorithm. The information learning is an operation of determining the property, rule, and determination reference of information, quantifying a relationship between information items, and predicting new data using the quantified pattern.

The machine learning technology may use an algorithm based on statistics, for example, a decision tree that uses a tree structure form as a predictive model, a neural network that emulates a structure and function of a neural network structure of a living organism, genetic programming based on an evolution algorithm of a living organism, clustering for distributing observed examples to subsets that are each a cluster, or a Monter carlo method of calculating a function value using probability through a random number that is arbitrarily extracted.

Deep learning technology that is one field of machine learning technology performs at least one of learning, determination, or processing of information using the neural network algorithm. The neural network may have a structure for connection between layers and transferring data between layers. The deep learning technology may learn a massive amount of information through a neural network using a graphic processing unit (GPU) that is optimized for parallel arithmetic.

The artificial intelligence part 130 may collect (percept, monitor, extract, detect, or receive) a signal, data, information, or the like, which is input or output from components of the mobile terminal in order to collect a massive amount of information for applying the machine learning technology. The artificial intelligence part 130 may collect (percept, monitor, extract, detect, or receive) data, information, or the like, which is stored in an external memory (e.g., a cloud server or a cloud server) connected via communication. In more detail, information collection may be understood to be a term including an operation of detecting information through a sensor, extracting information stored in the memory 170, or receiving information from the external memory via communication.

The artificial intelligence part 130 may detect information in the mobile terminal, information on an environment around the mobile terminal, and user information through the sensing unit 140. The artificial intelligence part 130 may receive broadcast signal, broadcast related information, wireless signal, and/or wireless data through the wireless communication unit 110. The artificial intelligence part 130 may receive image information (or a signal), audio information (or a signal), and data from an input interface, or information input from a user.

The artificial intelligence part 130 may collect a massive amount of information in real time on a background, may learn the information, and may store information (e.g., a knowledge graph, a command policy, a personalized database, a chat engine, or the like) processed in a proper form, in the memory 170.

When an operation of the mobile terminal is predicted based on learned information using the machine learning technology, the artificial intelligence part 130 may control components of the mobile terminal or may transfer a control command for executing the predicted operation to the controller 180 in order to perform the predicted operation. The controller 180 may control the mobile terminal based on the control command and may perform the predicted operation.

When a specific operation is performed, the artificial intelligence part 130 may analyze history information indicating that the specific information is performed and may update existing learned information based on the analyzed information through the machine learning technology. Thus, the artificial intelligence part 130 may increase the accuracy of predicting information.

In the specification, the artificial intelligence part 130 and the controller 180 may be understood to be the same component. In this case, the function perform by the controller 180 described in the specification may be expressed as being performed by the artificial intelligence part 130, and the controller 180 may also be referred to as the artificial intelligence part 130, or conversely, the artificial intelligence part 130 may also be referred to as the controller 180.

In contrast, in the specification, the artificial intelligence part 130 and the controller 180 may be understood to be separate components. In this case, the artificial intelligence part 130 and the controller 180 may variously perform control on the mobile terminal by exchanging data with each other. The controller 180 may perform at least one function on the mobile terminal or may control at least one of components of the mobile terminal, based on the result derived from the artificial intelligence part 130. In addition, the artificial intelligence part 130 may also be operated under control of the controller 180.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output interface 150 is typically configured to output various types of information, such as audio, video, tactile output, and the like. The output interface 150 is shown having a display 151, an audio output module 152, a haptic module 153, and an optical output module 154. The display 151 may have an inter-layered structure or an integrated structure with a touch sensor in order to facilitate a touch screen. The touch screen may provide an output interface between the mobile terminal 100 and a user, as well as function as the user input interface 123 which provides an input interface between the mobile terminal 100 and the user.

The interface 160 serves as an interface with various types of external devices that can be coupled to the mobile terminal 100. The interface 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the above-described components, or activating application programs stored in the memory 170.

In addition, the controller 180 controls at least some of the components illustrated in FIG. 1A, in order to execute the application program stored in the memory 170. Further, the controller 180 may operate a combination of at least two of the components included in the mobile terminal 100, in order to execute the application program.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Hereinafter, prior to description of various embodiments implemented via the above-described mobile terminal 100, the above-described components will be described in greater detail with reference to FIG. 1A.

Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The broadcast managing entity may be a server which generates and transmits a broadcast signal and/or broadcast associated information, or a server which receives a pre-generated broadcast signal and/or broadcast associated information, and sends such items to the mobile terminal. The broadcast signal may be implemented using any of a TV broadcast signal, a radio broadcast signal, a data broadcast signal, and combinations thereof, among others. The broadcast signal in some cases may further include a data broadcast signal combined with a TV or radio broadcast signal.

The broadcast signal may be encoded according to any of a variety of technical standards or broadcasting methods (for example, International Organization for Standardization (ISO), International Electrotechnical Commission (IEC), Digital Video Broadcast (DVB), Advanced Television Systems Committee (ATSC), and the like) for transmission and reception of digital broadcast signals. The broadcast receiving module 111 can receive the digital broadcast signals using a method appropriate for the transmission method utilized.

Examples of broadcast associated information may include information associated with a broadcast channel, a broadcast program, a broadcast event, a broadcast service provider, or the like. The broadcast associated information may also be provided via a mobile communication network, and in this case, received by the mobile communication module 112.

The broadcast associated information may be implemented in various formats. For instance, broadcast associated information may include an Electronic Program Guide (EPG) of Digital Multimedia Broadcasting (DMB), an Electronic Service Guide (ESG) of Digital Video Broadcast-Handheld (DVB-H), and the like. Broadcast signals and/or broadcast associated information received via the broadcast receiving module 111 may be stored in a suitable device, such as a memory 170.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to the mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input interface 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input interface 123 is a component that permits input by a user. Such user input may enable the controller 180 to control operation of the mobile terminal 100. The user input interface 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, the controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display 151, or convert capacitance occurring at a specific part of the display 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display 151 is generally configured to output information processed in the mobile terminal 100. For example, the display 151 may display execution screen information of an application program executing at the mobile terminal 100 or user interface (UI) and graphic user interface (GUI) information in response to the execution screen information.

In some embodiments, the display 151 may be implemented as a stereoscopic display for displaying stereoscopic images. A typical stereoscopic display may employ a stereoscopic display scheme such as a stereoscopic scheme (a glass scheme), an auto-stereoscopic scheme (glassless scheme), a projection scheme (holographic scheme), or the like.

In general, a 3D stereoscopic image may include a left image (e.g., a left eye image) and a right image (e.g., a right eye image). According to how left and right images are combined into a 3D stereoscopic image, a 3D stereoscopic imaging method can be divided into a top-down method in which left and right images are located up and down in a frame, an L-to-R (left-to-right or side by side) method in which left and right images are located left and right in a frame, a checker board method in which fragments of left and right images are located in a tile form, an interlaced method in which left and right images are alternately located by columns or rows, and a time sequential (or frame by frame) method in which left and right images are alternately displayed on a time basis.

Also, as for a 3D thumbnail image, a left image thumbnail and a right image thumbnail can be generated from a left image and a right image of an original image frame, respectively, and then combined to generate a single 3D thumbnail image. In general, the term "thumbnail" may be used to refer to a reduced image or a reduced still image. A generated left image thumbnail and right image thumbnail may be displayed with a horizontal distance difference there between by a depth corresponding to the disparity between the left image and the right image on the screen, thereby providing a stereoscopic space sense.

A left image and a right image required for implementing a 3D stereoscopic image may be displayed on the stereoscopic display using a stereoscopic processing unit. The stereoscopic processing unit can receive the 3D image and extract the left image and the right image, or can receive the 2D image and change it into a left image and a right image.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface 160 serves as an interface for external devices to be connected with the mobile terminal 100. For example, the interface 160 can receive data transmitted from an external device, receive power to transfer to elements and components within the mobile terminal 100, or transmit internal data of the mobile terminal 100 to such external device. The interface 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface 160.

When the mobile terminal 100 is connected with an external cradle, the interface 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

Here, the terminal body may be understood as referring to the mobile terminal 100 as at least one assembly.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display 151 is shown located on the front side of the terminal body to output information. As illustrated, a window 151a of the display 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

The mobile terminal includes a display 151, a first and a second audio output modules 151a/151b, a proximity sensor 141, an illumination sensor 142, an optical output module 154, a first and a second cameras 121a/121b, a first and a second manipulation units 123a/123b, a microphone 122, interface 160 and the like.

It will be described for the mobile terminal as shown in FIGS. 1B and 1C. The display 151, the first audio output module 151a, the proximity sensor 141, an illumination sensor 142, the optical output module 154, the first camera 121a and the first manipulation unit 123a are arranged in front surface of the terminal body, the second manipulation unit 123b, the microphone 122 and interface 160 are arranged in side surface of the terminal body, and the second audio output modules 151b and the second camera 121b are arranged in rear surface of the terminal body.

However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display 151 displays (outputs) information processed in the mobile terminal 100. The display 151 may execution screen information of an application program executed on the mobile terminal 100 or user interface (UI) or graphical user interface (GUI) information according to such execution screen information.

Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display 151 may be implemented using two display devices, which can implement the same or different display technology. For instance, a plurality of the displays 151 may be arranged on one side, either spaced apart from each other, or these devices may be integrated, or these devices may be arranged on different surfaces.

The display 151 may also include a touch sensor which senses a touch input received at the display. When a touch is input to the display 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display 151 may also form a touch screen together with the touch sensor. Here, the touch screen may serve as the user input interface 123 (see FIG. 1A). Therefore, the touch screen may replace at least some of the functions of the first manipulation unit 123a.

The first audio output module 152a may be implemented in the form of a speaker to output voice audio, alarm sounds, multimedia audio reproduction, and the like.

The window 151a of the display 151 will typically include an aperture to permit audio generated by the first audio output module 152a to pass. One alternative is to allow audio to be released along an assembly gap between the structural bodies (for example, a gap between the window 151a and the front case 101). In this case, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output interface 154 to stop the light output.

The first camera 121a can process image frames such as still or moving images obtained by the image sensor in a capture mode or a video call mode. The processed image frames can then be displayed on the display 151 or stored in the memory 170.

The first and second manipulation units 123a and 123b are examples of the user input interface 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display 151, or the like.

As another example of the user input interface 123, a rear input interface (not shown) may be located on the rear surface of the terminal body. The rear input interface can be manipulated by a user to provide input to the mobile terminal 100. The input may be used in a variety of different ways. For example, the rear input interface may be used by the user to provide an input for power on/off, start, end, scroll, control volume level being output from the first or second audio output modules 152a or 152b, switch to a touch recognition mode of the display 151, and the like. The rear input interface may be configured to permit touch input, a push input, or combinations thereof.

The rear input interface may be located to overlap the display 151 of the front side in a thickness direction of the terminal body. As one example, the rear input interface may be located on an upper end portion of the rear side of the terminal body such that a user can easily manipulate it using a forefinger when the user grabs the terminal body with one hand. Alternatively, the rear input interface can be positioned at most any location of the rear side of the terminal body.

Embodiments that include the rear input interface may implement some or all of the functionality of the first manipulation unit 123a in the rear input interface. As such, in situations where the first manipulation unit 123a is omitted from the front side, the display 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display 151 or implemented in the user input interface 123.

The microphone 122 is shown located at an end of the mobile terminal 100, but other locations are possible. If desired, multiple microphones may be implemented, with such an arrangement permitting the receiving of stereo sounds.

The interface 160 may serve as a path allowing the mobile terminal 100 to interface with external devices. For example, the interface 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

As shown in FIG. 1C, a flash 124 is shown adjacent to the second camera 121b. When an image of a subject is captured with the camera 121b, the flash 124 may illuminate the subject.

As shown in FIG. 1B, the second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body.

The battery 191 may receive power via a power source cable connected to the interface 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display 151 to extend the function of the mobile terminal 100. Another example of the accessory is a touch pen for assisting or extending a touch input to a touch screen.

In the present disclosure, information processed in the mobile terminal may be displayed using a flexible display. Hereinafter, this will be described in greater detail with reference to the accompanying drawings.

Hereinafter, embodiments related to a control method which may be implemented in the above-described mobile terminal will be described with reference to the accompanying drawings. It is apparent to those skilled in the art that the present disclosure can be embodied in other specific forms without departing from the spirit and essential features of the present disclosure.

In this specification, the term memory 170 may be used interchangeably with the term storage unit 170.

The mobile terminal 100 may include a communication unit composed of the wireless communication unit 110 and the interface 160.

The controller 180 may control operation of each component of the mobile terminal 100 under control of the artificial intelligence part 130.

The input unit 120 of the mobile terminal 100 may include the sensing unit 140, and perform all functions performed by the sensing unit 140. For example, the input unit 120 may detect user touch input.

Hereinafter, a mobile terminal will be described as an embodiment of the present disclosure. However, the present disclosure is not limited thereto and is applicable to all terminals or electronic apparatuses having an artificial intelligence function.

That is, the mobile terminal described with reference to FIG. 1 is merely an example of a terminal capable of implementing the present disclosure. Accordingly, the terminal, to which the present disclosure is applied, may not be a mobile terminal. In addition, the terminal, to which the present disclosure is applied, may include some or all of the components described with reference to FIG. 1.

Figure 2:
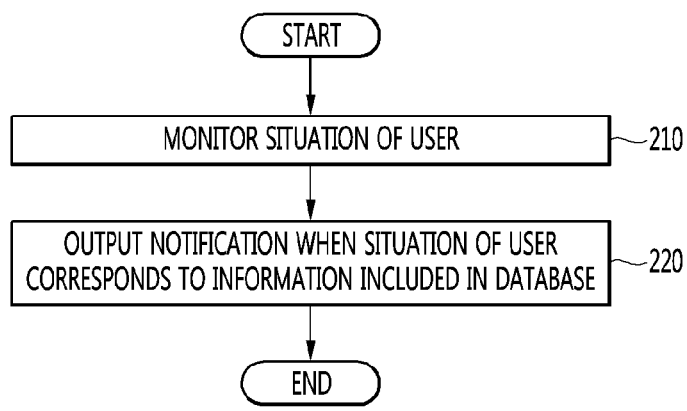
FIG. 2 is a view illustrating a method of operating a terminal according to an embodiment of the present disclosure.

FIG. 2 is a view illustrating a method of operating a terminal according to an embodiment of the present disclosure.

In FIG. 2, the method of operating the terminal according to the embodiment of the present disclosure may include step S210 of acquiring information on the situation of a user and step of outputting a notification when the situation of the user corresponds to information included in a database.

The terminal 310 may include at least one of an output unit, a storage unit, a situation information acquisition unit, a communication unit, a controller or an artificial intelligence part.

For the output unit of the terminal 310, refer to the description of the output unit 150 of the mobile terminal 100 described with reference to FIG. 1.

The output unit may output a notification. The notification may be to provide a guide to a user's behavior and may be output using various methods.

For example, the output unit may visually display the notification, audibly output the notification, output the notification using a haptic signal or output the notification using a combination of the above-described methods.

For the storage unit of the terminal 310, refer to the description of the storage unit 180 of the mobile terminal 100 described with reference to FIG. 1.

The storage unit may store various types of data or programs necessary to drive the terminal.

In addition, the storage unit may store a database. Here, the database may include at least one of a user's personal database, a standard behavior database or an accident type database.

For the situation information acquisition unit of the terminal 310, refer to the description of the wireless communication unit 110, the input unit 120 and the sensing unit 140 of the mobile terminal 100 described with reference to FIG. 1.

The situation information acquisition unit may collect data necessary to determine the situation of the user. In this case, the artificial intelligence part may acquire information on the situation of the user based on the data acquired by the situation information acquisition unit.

For the communication unit, refer to the description of the wireless communication unit 110 and the interface 160 of the mobile terminal 100 described with reference to FIG. 1.

The communication unit may communicate with one or more external apparatus. For example, if the terminal configures a driver guide system, the communication unit may communicate with at least one of a driver recognition device, a behavior detection device, a driving state detection device or a display device.

For the controller, refer to the description of the controller 180 of the mobile terminal 100 described with reference to FIG. 1.

The controller may control overall operation of the terminal. Specifically, the controller may control operation of at least one of the output unit, the storage unit, the situation information acquisition unit, the communication unit or the artificial intelligence part.

For the artificial intelligence part, refer to the description of the artificial intelligence part 130 of the mobile terminal 100 described with reference to FIG. 1.

The artificial intelligence part may output a notification when the situation of the user corresponds to information included in the database.

The notification may be output via the output unit or an output device 350. Specifically, the artificial intelligence part may control the output unit of the terminal 310 to output the notification. In addition, the artificial intelligence part may control the output device 350 to output the notification, by transmitting a notification output signal to the output device 350.

The artificial intelligence part may directly control the output unit to output the notification or the artificial intelligence part may control a controller for controlling output of the notification to output the notification.

Figure 3:
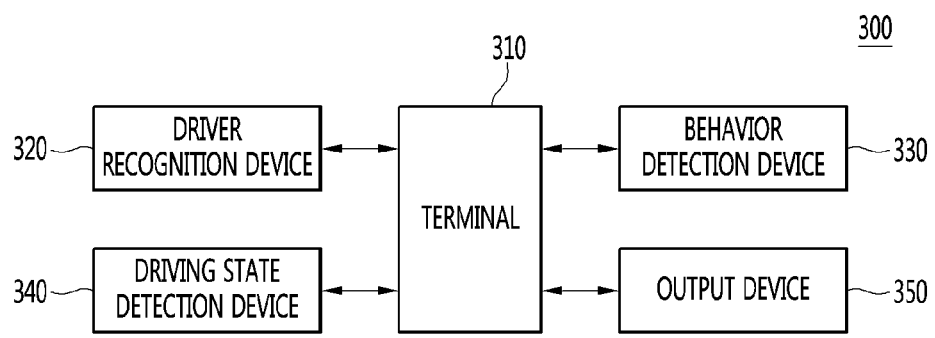
FIG. 3 is a view illustrating a driver guide system including a terminal according to an embodiment of the present disclosure.

FIG. 3 is a view illustrating a driver guide system including a terminal according to an embodiment of the present disclosure.

In FIG. 3, the driver guide system 300 may include a terminal 310. In addition, the driver guide system 300 may include at least one of a driver recognition device 320, a behavior detection device 300, a driving state detection device 340 or a display device 350.

The driver recognition device 320, the behavior detection device 300, the driving state detection device 340 and the display device 350 may be mounted in a vehicle.

The terminal 310 configuring the driver guide system 300 may be the mobile terminal 100 described with reference to FIG. 1, and, if a user carrying the mobile terminal 100 rides in the vehicle, the mobile terminal 100 may perform wireless communication with the driver recognition device 320, the behavior detection device 330, the driving state detection device 340 and the display device 350.

For the driver recognition device 320, the behavior detection device 330, the driving state detection device 340 and the display device 350, refer to some or all of the components of the mobile terminal 100 described with reference to FIG. 1.

The driver recognition device 320 may acquire data for determining who the driver is. Specifically, the driver recognition device 320 may collect unique information of a key of each driver, the fingerprint, grip, size and temperature of the driver's hand when each driver grabs a handle in order to open the door of the vehicle, iris recognition information, retina recognition information, speech recognition information, etc. In addition, the driver recognition device 320 may capture the image of the driver to acquire facial recognition information.

To this end, the driver recognition device 320 may include a camera, a microphone, a fingerprint scanner, an iris scanner, a retina scanner, a sensing device such as a temperature sensor, etc.

In this case, the driver recognition device 320 may transmit the acquired data to the terminal 310. In addition, the artificial intelligence part of the terminal 310 may determine who is driving based on the received data.

The behavior detection device 330 may acquire data for determining the behavior of the user. Specifically, the behavior detection device 330 may include one or more cameras and one or more cameras may capture the image of the user to acquire behavior information.

In addition, the behavior detection device 300 may transmit the acquired data to the terminal 310. In this case, the artificial intelligence part of the terminal 310 may determine what the behavior of the user is based on the received data.

The driving state detection device 340 may acquire data for determining the driving state of the vehicle.

Specifically, the driving state detection device 340 may capture the image of the surroundings of the vehicle.

In addition, the driving state detection device 340 may include a GPS module for acquiring the position of the vehicle.

In addition, the driving state detection device 340 may sense a signal related to driving of the vehicle 100. To this end, the sensing unit 130 may include a collision sensor, a wheel sensor, a speed sensor, an inclination sensor, a weight sensor, a heading sensor, a yaw sensor, a gyro sensor, a position module, a vehicle forward/reverse sensor, a battery sensor, a fuel sensor, a tire sensor, a steering sensor according to a steering wheel rotation, a vehicle inside-temperature sensor, a vehicle inside-humidity sensor, an ultrasonic sensor, a radar, a lidar, etc.

Accordingly, based on the data acquired by the driving state detection device 340, the artificial intelligence part of the terminal 310 may acquire vehicle collision information, vehicle direction information, vehicle location information, vehicle angle information, vehicle speed information, vehicle acceleration information, vehicle slope information, vehicle forward/reverse information, battery information, fuel information, tire information, vehicle lamp information, vehicle inside-temperature information, vehicle inside-humidity information, lane change information, etc.

The output device 350 outputs information processed in the terminal 310 and may include at least one of a display, a sound output unit or a haptic output unit.

The display of the output device 350 may display information processed in the terminal 310. For example, the display of the output device 350 may display the notification output from the terminal 310.

The display of the output device 350 may include at least one of a liquid crystal display (LCD), a thin film transistor-liquid crystal display (TFT LCD), an organic light-emitting diode (OLED), a flexible display, a three-dimensional 3D) display, or an e-ink display.

The display of the output device 350 may have an inter-layered structure or an integrated structure with a touch sensor so as to implement a touchscreen. The touchscreen may provide an output interface between the vehicle and a user, as well as functioning as the input unit which provides an input interface between the vehicle and the user. In this case, the display of the output device 350 may include a touch sensor for detecting touch of the display 141 to receive a control command using a touch method. Using this, when the display of the output device 350 is touched, the touch sensor detects the touch and the terminal 310 may generate a control command corresponding to the touch. Content input using the touch method may be characters or numbers or a menu item indicated or designated in various modes.

The display of the output device 350 may be implemented as a head up display (HUD). If the display of the output device 350 is implemented as a HUD, information may be output via a transparent display provided in a windshield. Alternatively, the display of the output device 350 may include a projection module to output information via an image projected onto the windshield.

The sound output unit of the output device 350 may convert the notification into sound and output the sound. Specifically, the sound output unit of the output device 350 may receive an electrical signal corresponding to the notification from the terminal 310, convert the received electrical signal into an audio signal, and output the audio signal. To this end, the sound output unit of the output device 350 may include a speaker, etc.

The haptic output unit of the output device 350 may generate tactile output corresponding to the notification. For example, the haptic output unit of the output device 350 may vibrate a steering wheel, a seat belt and a seat such that the user recognizes the output.

The terminal 310 may include some or all of the components of the driver recognition device 320, the behavior detection device 330 and the driving state detection device 340 described with reference to FIG. 3. In addition, the terminal 310 may perform the functions of the driver recognition device 320, the behavior detection device 330 and the driving state detection device 340 described with respect to FIG. 3.

For example, the terminal 310 may acquire data for determining the behavior of the user or data for determining who the driver is, by capturing the image of the driver.

The terminal 310 may communicate with the devices 320, 330, 340 and 350 configuring the driver guide system 300 via the communication unit of the terminal 310 and control overall operation of the devices 320, 330, 340 and 350 configuring the driver guide system 300.

In addition, the artificial intelligence part of the terminal 310 may receive data from the devices 320, 330, 340 and 350 configuring the driver guide system 300 and acquire information on the situation of the user based on the received data.

In addition, the artificial intelligence part of the terminal 310 may transmit a signal corresponding to the notification to the output device 350 based on the situation of the user. The output device 350 may output the notification based on the received signal.

In this specification, "the terminal 310 outputting the notification" or "the artificial intelligence part outputting the notification" may mean that the artificial intelligence part controls the output unit of the terminal 310 such that the notification is output from the terminal 310 or the artificial intelligence part transmits the signal corresponding to the notification to the output device 350 such that the notification is output from the terminal 310.

In this specification, "the artificial intelligence part acquiring the information on the situation of the user" may mean that the information on the situation of the user is acquired based on at least one of the data received from the other devices 320, 330, 340 and 350 configuring the system 300 or the data acquired by the situation information acquisition unit of the terminal 310.

Figure 4:
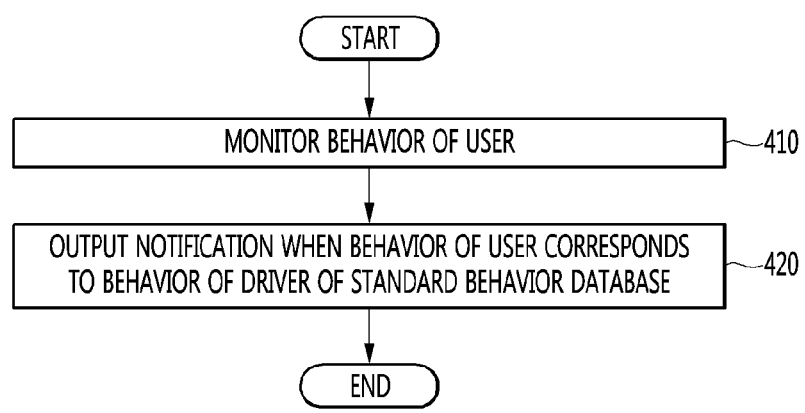
FIGS. 4 to 5 are views illustrating a method of outputting a notification according to a user's behavior according to an embodiment of the present disclosure.
Figure 5:
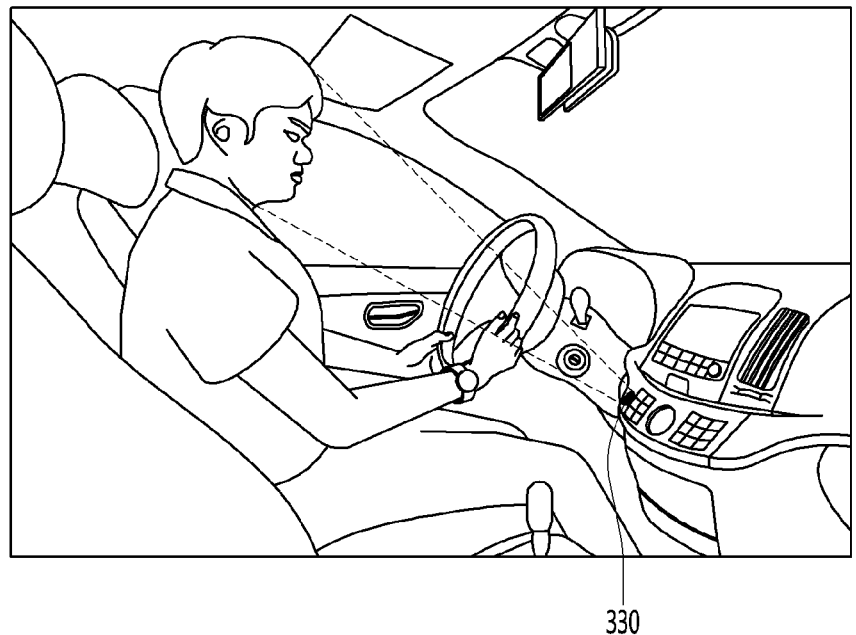

FIGS. 4 to 5 are views illustrating a method of outputting a notification according to a user's behavior according to an embodiment of the present disclosure.

The method of operating the terminal 310 according to the embodiment of the present disclosure may include step S410 of acquiring information on the behavior of a user and step S420 of outputting a notification when the behavior of the user corresponds to the behavior of a driver included in a standard behavior database.

Step S410 of acquiring the information on the behavior of the user will now be described.

The artificial intelligence part of the terminal 310 may acquire information on the situation of the user. Specifically, the artificial intelligence part of the terminal 310 may acquire the information on the behavior of the user.

Specifically, based on at least one of the data received from the other devices 320, 330, 340 and 350 configuring the system 300 or the data acquired by the situation information acquisition unit of the terminal 310, the artificial intelligence part may acquire the information on the behavior of the user.

For example, when the driving state detection device detects lane change of a vehicle and turn-on of a turn signal, the artificial intelligence part may determine that operation of turning on the turn signal is late when the user changes a lane based on a lane change time and a turn-on time of the turn signal.

In another example, when the driving state detection device detects lane change of a vehicle and the situation information acquisition unit photographs or films user's operation of turning on the turn signal, the artificial intelligence part may determine that user's operation of turning on the turn signal is late when the user changes a lane, based on a lane change time and a time when operation of turning on the turn signal is photographed or filmed.

In another example, when the behavior detection device 330 captures the image of the user, the artificial intelligence part may determine that the user does not view a rearview mirror for a predetermined time or more based on the captured image.

In FIG. 5, the behavior detection device 330 for capturing the image of the user is shown.

A database may be stored in the storage unit of the terminal 310.

Here, the database may include a standard behavior database.

The standard behavior database may include information on the behavior of the driver while driving. Here, the information on the behavior of the driver while driving may be information obtained by collecting the behaviors of the drivers when a plurality of accidents occurs.

Specifically, a standard behavior database provider may acquire the image of the driver captured by the behavior detection device 330 when an accident occurs. When such images are acquired from the plurality of accident cases, the standard behavior database provider may analyze the behavior pattern of the driver when an accident occurs and generate the standard behavior database including information on the behavior of the driver while driving. Meanwhile, the controller may receive the standard behavior database from the standard behavior database provider and store the standard behavior database in the storage unit.

For example, from a plurality of accident cases, it may be derived that a behavior of watching a smartphone while driving causes an accident. In this case, information on the behavior of the driver while driving may be information on the behavior of watching the smartphone while driving.

In another example, from a plurality of accident cases, it may be derived that a behavior of viewing a passenger seat without keeping eyes forward causes an accident. In this case, information on the behavior of the driver while driving may be information on the behavior of viewing the passenger seat without keeping eyes forward.

Although the behavior of the driver while driving is described as being acquired from the plurality of accident cases, the behavior of the driver while driving is not limited thereto and may be a behavior set by the standard behavior database provider. For example, the standard behavior database provider may set a behavior of driving while drowsy as the information on the behavior of the driver while driving.

In addition, the behavior of the driver while driving may be set by referring to a law. For example, if the behavior of watching the smartphone while driving violates the traffic regulations, the behavior of watching the smartphone may be set as the information on the behavior of the driver while driving.

Although the behavior of the driver while driving is described as being acquired from the captured image of the driver, the behavior of the driver while driving is not limited thereto and may be acquired from the statement of the accident party or the result of investigation of the police.

Step S420 of outputting the notification when the behavior of the user corresponds to the behavior of the driver included in the standard behavior database will now be described.

The artificial intelligence part may output the notification when the situation of the user corresponds to the information included in the database. Specifically, the artificial intelligence part may output the notification when the behavior of the user corresponds to the behavior of the driver included in the standard behavior database.

For example, when the artificial intelligence part determines that the user is currently drowsy based on the behavior of the user and the standard behavior database includes information on the drowsy behavior of the driver, the artificial intelligence part may output a warning notification.

In another example, when the artificial intelligence part determines that operation of turning on the turn signal when the user changes the lane is late and the standard behavior database includes the information on the behavior of turning on the turn signal late, the artificial intelligence part may output the warning notification.

The user may unconsciously or consciously behave dangerously while driving. When such a behavior occurs, the artificial intelligence part may warn the user, thereby providing a guide to user's safe driving. In particular, by comparing the standard behavior database acquired from the plurality of accident cases with the current behavior of the user, a more realistic guide is possible and the user may be warned.

Meanwhile, although the notification is described as being output based on the behavior of the user in the above-described embodiment, the notification may be output in consideration of the position of the user in addition to the behavior of the user.

Specifically, the standard behavior database may include information on a position and information on the behavior of the driver at the position. Here, the information on the behavior of the driver while driving may be obtained by collecting the behaviors of the drivers when a plurality of accidents occurs at the position.

Specifically, in the standard behavior database provider, when accidents occurs at various positions, the behavior detection device 330 may acquire the captured images of the drivers. When such images are acquired from the plurality of accident cases, the standard behavior database provider may analyze the behavior pattern of the driver when accidents occur at various positions and generate the standard behavior database including information on the behaviors of the drivers at the plurality of positions. Meanwhile, the controller may receive the standard behavior database from the standard behavior database provider and store the standard behavior database in the storage unit.

For example, from the plurality of accident cases, it may be derived that the pattern of the driver's behavior of looking to the right at a first position may cause an accident (for example, when the driver passes the first position, since there is a beautiful building in a right direction, the driver may frequently look to the right and thus an accident may frequently occur. In this case, information included in the standard behavior database may be the position information of the first position and information on the driver's behavior of looking to the right.

In another example, from the plurality of accident cases, it may be derived that the driver does not turn on the turn signal at a second position when changing the lane to the left, thereby causing an accident. In this case, information included in the standard behavior database may be the position information of the second position and information on the driver's behavior of not turning on the turn signal at the second position.

The position included in the database may be a position where a vehicle accident frequently occurs.

Meanwhile, operation performed by the standard behavior database provider may be performed by the artificial intelligence part of the terminal 310.

The artificial intelligence part of the terminal 310 may receive information on the position of the user via the communication unit of the terminal 310 or from the driving state detection device 340 and acquire the information on the position of the user.

In addition, the artificial intelligence part of the terminal 310 may output the notification when the user passes the position included in the standard behavior database and the behavior of the user corresponds to the behavior of the driver at the position.

For example, when the artificial intelligence part determines that the current position of the user is a first position and the user is drowsy based on the behavior of the user and the standard behavior database includes the first position and information on the driver's drowsy behavior at the first position, the artificial intelligence part may output the warning notification.

In the above-described embodiment, the notification is described as being output when the user passes the position. Passing through the position may include not only passing the position but also being going to pass the position.

For example, when the first position is a specific intersection and the user is driving toward the specific intersection, the artificial intelligence part may output the notification at a predetermined time before entering the specific intersection (or at a predetermined distance before the specific intersection).

The patterns of accidents occurring at specific positions may not be standardized. For example, when a sea suddenly appears on the left side, drivers may look to the left, thereby causing a lot of accidents. In another example, drivers who are driving on a straight road are in a drowsy state, thereby causing a lot of accidents.

In the present disclosure, by comparing behaviors causing accidents at specific positions with the current behavior of the user and providing a guide to the behavior of the user, it is possible to prevent an accident by a standardized pattern at the specific position.

The standard behavior database may include information on an incorrect behavior of a driver while driving. For example, the standard behavior database may include information on the behavior of the driver acquired from the plurality of accident cases, information on the behavior of the driver set by the standard behavior database provider, etc.

The storage unit may include information on a correct behavior corresponding to the incorrect behavior of the driver.

For example, the standard behavior database may include a driver's behavior of driving while drowsy, and information on a behavior such as "Do not drowse", "Why don't you open a window and stretch in order to keep you awake?" or "Stop by a rest area for a cup of coffee" may be stored in the storage unit.

The artificial intelligence part may output a correct behavior when the behavior of the user corresponds to the incorrect behavior of the driver.

For example, when the artificial intelligence part determines that the user is currently drowsy based on the behavior of the user and the standard behavior database includes information on the drowsy behavior of the driver, the artificial intelligence part may output a correct behavior "Stop by a rest area for a cup of coffee".

Figure 6:
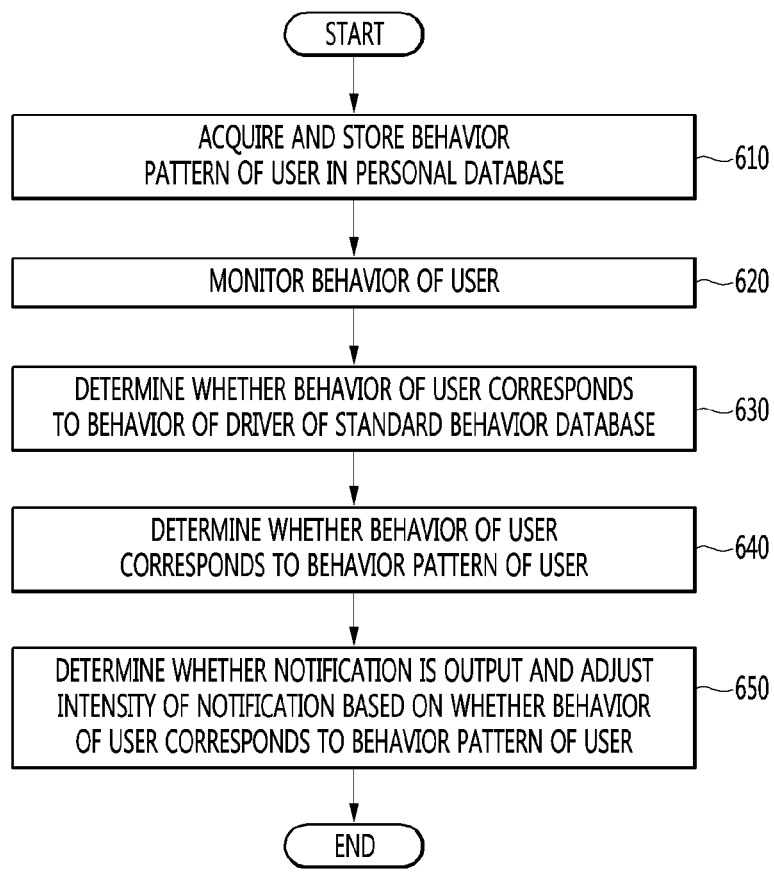
FIG. 6 is a view illustrating a method of determining whether a notification is output and the intensity of the notification in consideration of the behavior pattern of a user according to an embodiment of the present disclosure.

FIG. 6 is a view illustrating a method of determining whether a notification is output and the intensity of the notification in consideration of the behavior pattern of a user according to an embodiment of the present disclosure.

The method of operating the terminal 310 according to the embodiment of the present disclosure may include step S610 of acquiring and storing the behavior pattern of a user in a personal database, step S620 of acquiring information on the behavior of the user, step S630 of determining whether the behavior of the user corresponds to the behavior of the driver of the standard behavior database, step S640 of determining whether the behavior of the user corresponds to the behavior pattern of the user when the behavior of the user corresponds to the behavior of the driver of the standard behavior database and step S650 of determining whether a notification is output or adjusting the intensity of the notification based on whether the behavior of the user corresponds to the behavior pattern of the user.

The database may include the personal database of the user.

Step S610 of acquiring and storing the behavior pattern of the user in the personal database will now be described.

Here, information on the situation of the user may be stored in the personal database of the user. Specifically, the artificial intelligence part may store information on the behavior of the user in the personal database of the user.

For example, the artificial intelligence part may store a user's behavior of not seeing a rearview mirror for a predetermined time or more, a behavior of turning on a turn signal late when changing a lane to the left, a user's behavior of looking to the right without keeping their eyes forward and a user's drowsy behavior in the personal database.

Meanwhile, the personal database of the user may include information on the behavior pattern of the user. The behavior pattern of the user may be acquired based on a plurality of past behaviors of the user.

Specifically, the artificial intelligence part may acquire the behavior pattern of the user, based on at least one of how often a specific behavior of the user appears, the number of times that the specific behavior of the user appears or a point in time when the specific pattern appears.

For example, when the number of times that the user's drowsy behavior appears is equal to or greater than a predetermined number or is one or more per month, the artificial intelligence part may determine the user's drowsy behavior as the behavior pattern of the user and store the determined behavior pattern in the personal database.

In another example, although the behavior pattern of the user includes a behavior of turning on the turn signal late one year ago, if that behavior have not appeared thereafter, the artificial intelligence part may exclude the behavior of turning on the turn signal late from the behavior pattern.

For step S620 of acquiring the information on the behavior of the user and step S630 of determining whether the behavior of the user corresponds to the behavior of the driver of the standard behavior database, refer to the description of FIGS. 4 to 5.

Step S640 of determining whether the behavior of the user corresponds to the behavior pattern of the user when the behavior of the user corresponds to the behavior of the driver of the standard behavior database will now be described.

When the behavior of the user corresponds to the behavior of the driver of the standard behavior database, the artificial intelligence part may determine whether the behavior of the user corresponds to the behavior pattern of the user.

For example, when the behavior of the user is currently a drowsy behavior and the behavior of the driver of the standard behavior database includes a drowsy behavior, the artificial intelligence part may determine whether the user's drowsy behavior is stored in the personal database as the behavior pattern of the user. When the user's drowsy behavior is stored in the personal database as the behavior pattern of the user, the artificial intelligence part may determine that the current behavior of the user corresponds to the behavior pattern of the user.

Step S650 of determining whether the notification is output or adjusting the intensity of the notification based on whether the behavior of the user corresponds to the behavior pattern of the user will now be described.

Based on whether the behavior of the user corresponds to the behavior pattern of the user, the artificial intelligence part may determine whether the notification is output.

For example, if the current behavior of the user is a behavior of not keeping eyes forward and the standard behavior database includes a behavior of not keeping eyes forward but the behavior of not keeping eyes forward is not the behavior pattern of the user, the artificial intelligence part may not output the notification.

Based on whether the behavior of the user corresponds to the behavior pattern of the user, the artificial intelligence part may adjust the output intensity of the notification. Specifically, the artificial intelligence part may output the notification with a low intensity or a high intensity based on whether the behavior of the user corresponds to the behavior pattern of the user.

For example, if the current behavior of the user is a behavior of not keeping eyes forward and the standard behavior database includes a behavior of not keeping eyes forward but the behavior of not keeping eyes forward is not the behavior pattern of the user, the artificial intelligence part may output the notification with a low intensity.

In another example, if the current behavior of the user is a behavior of not keeping eyes forward, the standard behavior database includes a behavior of not keeping eyes forward, and the behavior of not keeping eyes forward is the behavior pattern of the user, the artificial intelligence part may output the notification with a high intensity.

The notification with the low intensity and the notification with the high intensity may be distinguished according to the level, frequency, etc.

For example, when the notification is audibly output, the notification with the low intensity may be output once every 5 seconds in a small voice and the notification with the high intensity may be output once every 2 seconds in a large voice.

In another example, if the notification is output as an image, the notification with the low intensity may be output in text having a small size and the notification with the high intensity may be output in text having a large size.

In another example, when the notification is output as a haptic signal, the notification with the low intensity may be output once every 5 seconds with a small vibration magnitude and the notification with the high intensity may be output once every 2 seconds with a large vibration magnitude.

Outputting the notification whenever the specific behavior of the user appears may cause fatigue to the user. Accordingly, the present disclosure has an advantage of outputting a warning only with respect to the bad habits of the user, by extracting the behavior pattern of the user from the behaviors of the user, determining whether the specific behavior of the user is the behavior pattern of the user, and outputting a warning.

In addition, the user is warned about a bad behavior even if the bad behavior is not the habit of the user. Accordingly, the present disclosure has an advantage of outputting a warning having a high intensity in case of a behavior originating from the habit of the user and outputting a warning having a low intensity in case of a bad behavior which is not the habit of the user, thereby weakly warning the user about a bad behavior which is not a habit and warning the user about a bad habit.

Although whether the notification is output or the intensity of the notification is described as being determined or adjusted based on whether the behavior of the user corresponds to the behavior pattern of the user in FIG. 6, the present disclosure is not limited thereto.

Specifically, the information on the behavior of the user is stored in the personal database of the user as described above, and the artificial intelligence part may determine whether the notification is output or adjust the intensity of the notification based on whether the behavior of the user corresponds to the behavior of the user included in the personal database.

For example, if the current behavior of the user is a behavior of not keeping eyes forward, the standard behavior database includes a behavior of not keeping eyes forward and the history of the user's behavior of not keeping eyes forward in the past is stored in the personal database of the user, the artificial intelligence part may output the notification with a higher intensity.

In another example, if the current behavior of the user is a behavior of not keeping eyes forward, and the standard behavior database includes a behavior of not keeping eyes forward, but the history of the user's behavior of not keeping eyes forward in the past is not stored in the personal database of the user, the artificial intelligence part may not output the notification or may be output the notification with a lower intensity.

Figure 7:
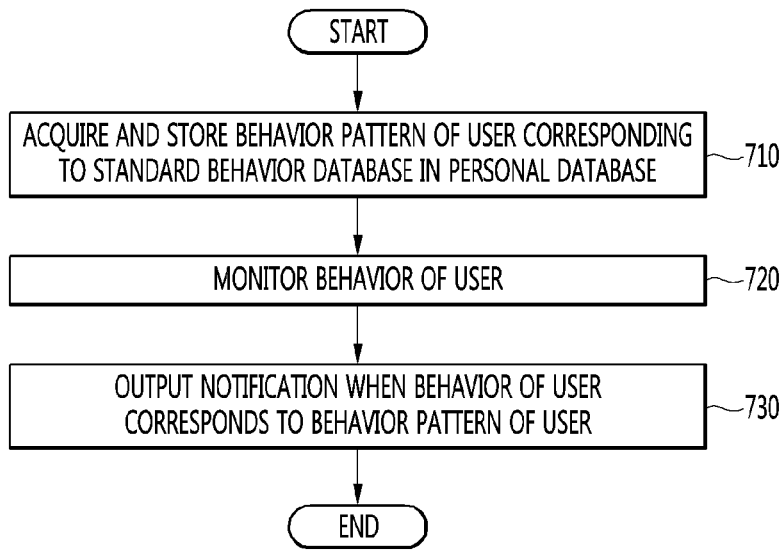
FIG. 7 is a view illustrating a method of outputting a notification using a behavior pattern of a user corresponding to a standard behavior database according to an embodiment of the present disclosure.

FIG. 7 is a view illustrating a method of outputting a notification using a behavior pattern of a user corresponding to a standard behavior database according to an embodiment of the present disclosure.

The method of operating the terminal 310 according to the embodiment of the present disclosure may include step S710 of acquiring the behavior pattern of the user corresponding to the standard behavior database based on the behavior of the user and the standard behavior database and storing the behavior pattern of the user in the personal database of the user, step S720 of acquiring the information on the behavior of the behavior of the user and step of outputting a notification when the behavior of the user corresponds to the behavior pattern of the user.

Step S710 of acquiring the behavior pattern of the user corresponding to the standard behavior database based on the behavior of the user and the standard behavior database and storing the behavior pattern of the user in the personal database of the user will now be described.

The artificial intelligence part may acquire the behavior pattern of the user corresponding to the standard behavior database based on the behavior of the user and the standard behavior database.

Specifically, the artificial intelligence part may acquire the information on the behavior of the user and store the acquired behavior of the user in the personal database of the user as the behavior pattern of the user when the behavior of the user corresponds to the behavior of the driver included in the standard behavior database.

The behavior pattern may be acquired based on how often the specific behavior of the user appears, the number of times that the specific behavior of the user appears or a point in time when the specific pattern appears. How often the specific behavior of the user appears, the number of times that the specific behavior of the user appears or the point in time when the specific pattern appears may be changed according to settings.

For example, even if the number of times that the user's behavior of not keeping eyes forward appears is only one, the user's behavior of not keeping eyes forward may be stored as the behavior pattern of the user. In another example, when the number of times that the user's behavior of not keeping eyes forward appears is equal to or greater than three, the user's behavior of not keeping eyes forward may be stored as the behavior pattern of the user. In addition, when the number of times that the user's behavior of not keeping eyes forward appears is equal to or greater than three and is greater than one per month, the user's behavior of not keeping eyes forward may be stored as the behavior pattern of the user.

The artificial intelligence part may acquire the information on the current behavior of the user and output the notification when the current behavior of the user corresponds to the behavior pattern stored in the personal database.

For example, when the behavior of not keeping eyes forward may be stored in the personal database of the user as the behavior pattern of the user and the current behavior of the user is the behavior of not keeping eyes forward, the artificial intelligence part may output the notification.

If the behavior of the user is compared with the standard behavior database whenever the behavior of the user appears, the bad habit of the user may be patterned and stored in advance. When the behavior of the user appears later, since the process of comparing the behavior of the user with the information patterned and stored in advance is only performed, it is possible to more rapidly provide a guide to the user.

Figure 8:
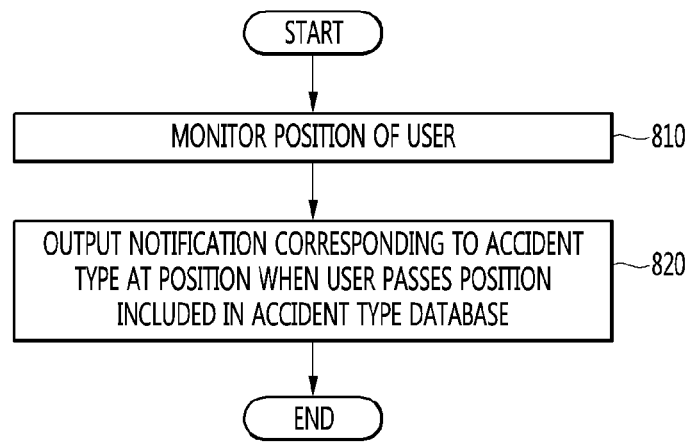

FIGS. 8 to 9 are views illustrating a method of outputting a notification based on an accident type database according to an embodiment of the present disclosure.

The accident type database may include information on a position and information on an accident type at the position. The information on the accident type may be collected when a plurality of accidents occurs at the position.

Specifically, an accident type database provider may acquire information including the type of the accident when accidents occur at various positions. When such information is acquired from a plurality of accident cases, the accident type database provider may analyze the patterns of the types of the accidents at various positions and generate the accident type database including the information on the types of the accidents at a plurality of positions.

For example, when a pattern in which accidents frequently occur at a first position due to rear collision of a rear vehicle is derived from the plurality of accident cases, the accident type database may include the first position and information on the rear collision at the first position.

In another example, when a pattern in which accidents frequently occur at a second position due to side collision while entering a left lane is derived from the plurality of accident cases, the accident type database may include the second position and information on left collision at the second position.

The controller may receive the accident type database from the accident type database provider and store the accident type database in the storage unit.

FIG. 9 shows a method of building the accident type database.

Information included in the accident type database may be acquired by receiving the images of an accident captured when the accident occurs from an insurance company or a police officer and analyzing the images.

In addition, the information included in the accident type database may be acquired by analyzing a document or data related to a traffic accident situation.

Operation performed by the accident type database provider may be performed by the artificial intelligence part of the terminal 310.

The method of operating the terminal 310 according to the embodiment of the present disclosure may include step S810 of acquiring information on the position of the user and step S820 of outputting a notification corresponding to the accident type at the position when the user passes the position included in the accident type database.

The artificial intelligence part may acquire information on the current position of the user based on the data collected by the driving state detection device or the situation information acquisition unit.

In addition, the artificial intelligence part may output the notification corresponding to the accident type at the position when the user passes the position included in the accident type database.

For example, if a first position and information on right collision at the first position are included in the accident type database, the artificial intelligence part may output a notification "Watch out for your right" when the user passes the first position.

In another example, if a second position and information on signal violation and speeding at the second position are included in the accident type database, the artificial intelligence part may output a notification "Watch out for signal violation and speeding" when the user passes the second position.

The user passing the position may include not only passing the position but also being going to pass the position.

Figure 10:
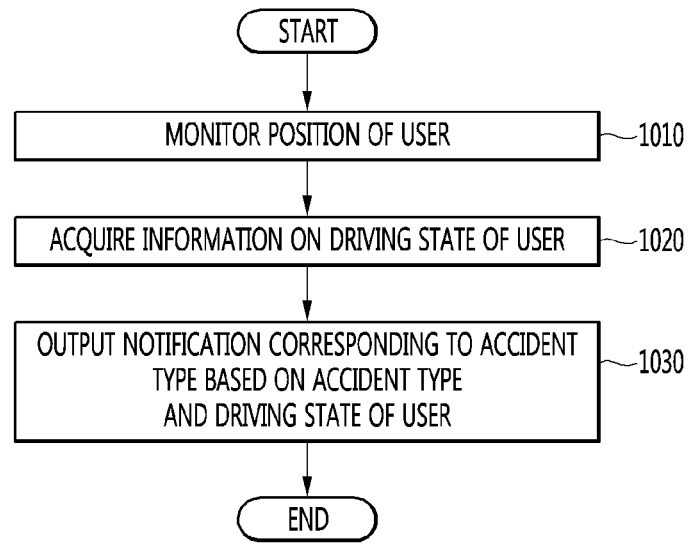
FIG. 10 is a view illustrating a method of outputting a notification corresponding to an accident type based on an accident type database and information on a driving state of a user according to an embodiment of the present disclosure.

FIG. 10 is a view illustrating a method of outputting a notification corresponding to an accident type based on an accident type database and information on a driving state of a user according to an embodiment of the present disclosure.

The method of operating the terminal 310 according to the embodiment of the present disclosure may include step S1010 of acquiring information on the position of the user, step S1020 of acquiring information on the driving state of the user, and step S1030 of outputting a notification corresponding to an accident type based on the driving state of the user and the accident type when the user passes a position included in the accident type database.

For step S1010 of acquiring the information on the position of the user, refer to the description of FIG. 8.

Step S1020 of acquiring the information on the driving state of the user will be described.

The artificial intelligence part may acquire the information on the driving state of the user based on the data acquired by the driving state detection device 340 or the data acquired by the situation information acquisition unit of the terminal 310.

The information on the driving state may include a vehicle direction, angle, speed, acceleration, inclination, forward/reverse, left turn/right turn, tire, vehicle lamp, lane, lane change information, neighboring vehicle information, etc.

Step of outputting the notification corresponding to the accident type based on the driving state of the user and the accident type when the user passes the position included in the accident type database will be described.

When the user passes the position included in the accident type database, the artificial intelligence part may output the notification corresponding to the accident type based on the driving state of the user and the accident type.

For example, if a first position and information on speeding at the first position are included in the accident type database and the speed of the vehicle is equal to or greater than a regulation speed, the artificial intelligence part may output a notification "Watch out for speeding" when the user passes the first position.

In addition, if a second position and information on left collision when the lane is changed from a third lane to a second lane at the second position are included in the accident type database and the vehicle travels in the third lane, the artificial intelligence part may output a notification "Watch out for your left".

Although the notification corresponding to the accident type is described as being output based on the driving state of the user and the accident type, the present disclosure is not limited thereto and the notification corresponding to the accident type may be output based on the behavior of the user and the accident type.

For example, if a third position and information on the type of an accident which changes a lane without turning on a turn signal at the third position are included in the accident type database, the artificial intelligence part may output a notification "Turn on a turn signal" based on information indicating that the user does not turn on the turn signal and the accident type.

The present disclosure has an advantage of guiding the user into safe driving, by analyzing the type of the accident at a specific position and outputting a notification according to the type of the accident.

In particular, by comparing the current driving state of the user with the accident type database acquired from a plurality of cases, it is possible to provide a more realistic guide.

Figure 11:
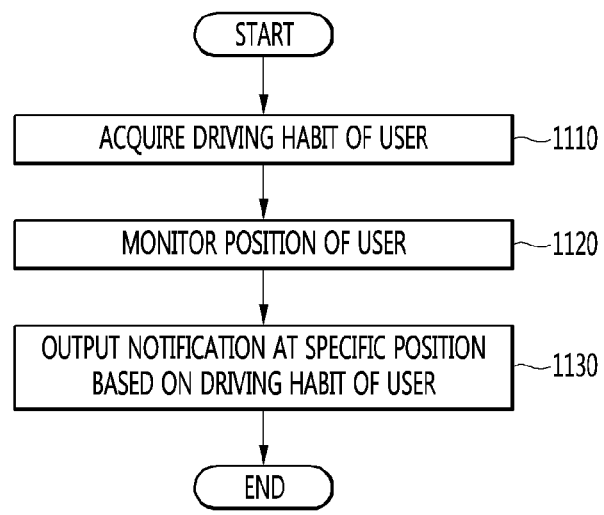
FIG. 11 is a view illustrating a method of guiding a user based on a driving habit of a user according to an embodiment of the present disclosure.

FIG. 11 is a view illustrating a method of guiding a user based on a driving habit of a user according to an embodiment of the present disclosure.

The method of operating the terminal 310 according to the embodiment of the present disclosure may include step S1110 of acquiring a driving habit of a user, step S1120 of acquiring information on a position of the user and step S1130 of outputting a notification related to the driving habit when the user reaches a position where the driving habit of the user appears.

Step S1110 of acquiring the driving habit of the user will be described.

The driving habit of the user is distinguished from the above-described behavior of the user and may mean a result of a behavior according to user's determination beyond a simple user's behavior.

Specifically, the driving habit may include traffic regulation violation information of the user.

The traffic regulation violation information of the user may be acquired by the artificial intelligence part.

For example, the artificial intelligence part may acquire information on the regulation speed of a road on which the user is located and determine whether the user violates the traffic regulations based on the regulation speed and the current speed of the user.

In another example, the artificial intelligence part may acquire information indicating that the user is turning left and information indicating that the user has not turned on the turn signal, and determine that the user has violated the traffic regulations based on the information indicating that the user is turning left and the information indicating that the user has not turned on the turn signal.

Although the traffic regulation violation information of the user is described as being acquired by the artificial intelligence part, the present disclosure is not limited thereto and the traffic regulation violation information of the user may be received from the traffic regulation violation information manager of a police server.

The driving habit may include route deviation information of the user.

The route deviation information may be acquired by the artificial intelligence part.

For example, when a specific route was set by navigation in the past and the user deviates from the specific route and then enters another route after following the specific route, the artificial intelligence part may determine that the user has deviated from the route. In this case, the artificial intelligence part may store information on the specific route and the other route.

In another example, when the navigation system performs route research once or plural times due to deviation from the route, the artificial intelligence part may determine that the user has deviated from the route.

In addition, the route deviation information may be acquired by the artificial intelligence part outputting a question to the user. Specifically, when a specific route is set by the navigation system and the user deviates from the specific route and enters another route after following the specific route, the artificial intelligence part may output a question as to whether the user has intentionally or inadvertently deviated from the route.

The terminal 310 may include an input unit capable of receiving the answer of the user. When an answer is received that the user has intentionally deviated from the route, the artificial intelligence part may store the other route in the personal database as the route, along which the user has traveled. In contrast, when an answer is received that the user has inadvertently deviated from the route, the artificial intelligence part may determine that the user has deviated from the route.

Meanwhile, when the driving habit of the user is acquired, the artificial intelligence part may store the driving habit and position information corresponding to the driving habit in the personal database.

The artificial intelligence part may acquire information on the current position of the user.

In addition, the artificial intelligence part may output a notification related to the driving habit at a position where the driving habit of the user appears, based on the driving habit of the user and position information corresponding to the driving habit.

Specifically, the artificial intelligence part may output a notification for preventing traffic regulation violation when reaching the position where the traffic regulation violation appears, based on the traffic regulation violation information and the position information corresponding to traffic regulation violation.

For example, when a driving habit such as speeding is acquired and speeding appears at a first position and a second position, the artificial intelligence part may output a notification "You speeded at the current point last time. Watch out for speeding" when the user reaches the first position or the second position.

In addition, the artificial intelligence part may output a notification for preventing route deviation when the user reaches a position where route deviation appears, based on the route deviation information and position information corresponding to route deviation.

For example, when the user deviates from a predetermined route at the first position, the artificial intelligence part may output a notification "You entered a road b without entering a road a at this point last time. Be careful", when the user reaches the first position.

"Position where the driving habit appears" may mean not only a position where the driving habit appears but also a position before reaching the position where the driving having appears.

For example, when the user has deviated from the first position in the past, the artificial intelligence part may determine that the user is going to the first position according to the route of the road and the movement direction of the user. In addition, the artificial intelligence part may output a notification for preventing route deviation at a predetermined time before reaching the first position (or at a predetermined distance before the first position).

The user may not remember their traffic regulation violation or route deviation and may repeat the same mistake. For example, the user mistaking a road and deviating from the route may repeatedly appear at the same position.

The present disclosure has an advantage of reminding the user of past mistakes by checking the driving habits of the user and outputting a warning using the same.

Although the notification for preventing traffic regulation violation is described as being output when there was a traffic regulation violation in the above-described embodiment, the present disclosure is not limited thereto.

Specifically, the artificial intelligence part may acquire a specific driving habit, e.g., the driving habit of the user which may potentially cause an accident. For example, the artificial intelligence part may acquire the driving habit of the user which is not a traffic regulation violation but may cause a dangerous situation. In addition, the artificial intelligence part may store a driving habit and position information corresponding to the driving habit. In this case, the artificial intelligence part may output a notification related to the driving habit at a position where the driving habit appears. For example, the artificial intelligence part may output a notification "There is a pedestrian crossing as soon as you cross this hill, so speeding on the hill like last time may be dangerous.

The artificial intelligence part may acquire a driving habit including the speed pattern of the user. In this case, the artificial intelligence part may output a notification for inducing the user to drive at an economic speed based on the driving habit of the user and the economic speed.

When the user uses a route used in the past again and the road condition of the used route has been changed, the artificial intelligence part may output a warning alarm. For example, the artificial intelligence part may output a notification "The speed limit of the road has been changed from 80 to 50 as compared to when you came last time.

The artificial intelligence part may output a notification to check tire pressure when the weather suddenly changes.

In addition, based on a previous vehicle checking timing, the artificial intelligence part may recommend a next vehicle checking timing.

The terminal 310 may output a notification based on who the user is.

Specifically, the storage unit may include a plurality of personal databases respectively corresponding to a plurality of users. For example, the behavior, behavior pattern and driving habit of a first user are stored in a first personal database corresponding to the first user and the behavior, behavior pattern and driving habit of a second user are stored in a second personal database corresponding to the second user.

In addition, when the user sits on a driver's seat, the artificial intelligence part of the terminal 310 may determine who the user sitting on the driver's seat is, output a notification based on a personal database corresponding to the user sitting on the driver's seat, and store information acquired while driving in the personal database corresponding to the user sitting on the driver's seat.

Behaviors or habits which occur while driving may differ between users. The present disclosure has an advantage of providing a driver-specific guide, by building a personal database of each user and guiding each user.

In addition, the artificial intelligence part of the terminal 310 may control the display position of an image based on who the user sitting on the driver's seat is.

Specifically, the artificial intelligence part of the terminal 310 may display an image at a position optimized for each user, which differs between users, based on the behavior pattern of the user.

For example, if the behavior pattern of a first user frequently sees a right 15-degree point, the artificial intelligence part of the terminal 310 may control the output device 350 such that an image is projected onto the right 15-degree point of the first user.

In another example, if the field of view of a second user is from left 30 degrees to right 30 degrees, the artificial intelligence part of the terminal 310 may control the output device 350 such that an image is projected within the field of view of the second user. In this case, the artificial intelligence part may change the display position of the image based on the field of view and movement speed of the user. For example, if the movement speed is high, since the field of view becomes narrower, the artificial intelligence part may display the image within a narrower field of view.

In another example, if a third user sees a left sideview mirror more often than a right sideview mirror, the artificial intelligence part may display major information of the vehicle on the right side of the screen.

The artificial intelligence part of the terminal 310 may transmit a control signal to a device capable of changing a sideview mirror, a rearview mirror, a seat, a song playlist, a recent destination for navigation, such that the driving environment corresponding to the user sitting on the driver's seat is created based on who the user sitting on the driver's seat is.

The artificial intelligence part of the terminal 310 may store conversation or saying goodbye when each user gets off the vehicle and output saying hello when the user rides in the vehicle.

In addition, the artificial intelligence part of the terminal 310 may output a preferred voice of each driver, such that the driver does not feel uncomfortable.

In addition, the artificial intelligence part may control a vehicle inside-temperature control system to maintain a preferred temperature of each driver.

In addition, the artificial intelligence part may provide the navigation history and recent destination to each driver.

Although the terminal is described as being the terminal 310 configuring the driver guide system 300 in FIGS. 2 to 11, the mobile terminal 100 described with reference to FIG. 1 will now be described.

FIGS. 12 to 15 are views illustrating a method of guiding a route based on a route pattern of a user according to an embodiment of the present disclosure.

The method of operating the terminal 310 according to the embodiment of the present disclosure may include step S1210 of storing the route, along which the user has moved, step S1220 of acquiring information on a movement route to be used by the user based on a past movement route of the user and current movement of the user, and step S1230 of providing a guide to a new route based on the route information of the route information to be used by the user.

Step S1210 of storing the route, along which the user has moved, will be described.

The artificial intelligence part 130 of the mobile terminal 100 may store information on the route, along which the user has moved.

Specifically, the artificial intelligence part 130 may store the information on the route, along which the user has moved, in the personal database of the user based on position information (e.g., GPS) acquired by the wireless communication unit 110.

Figure 13:
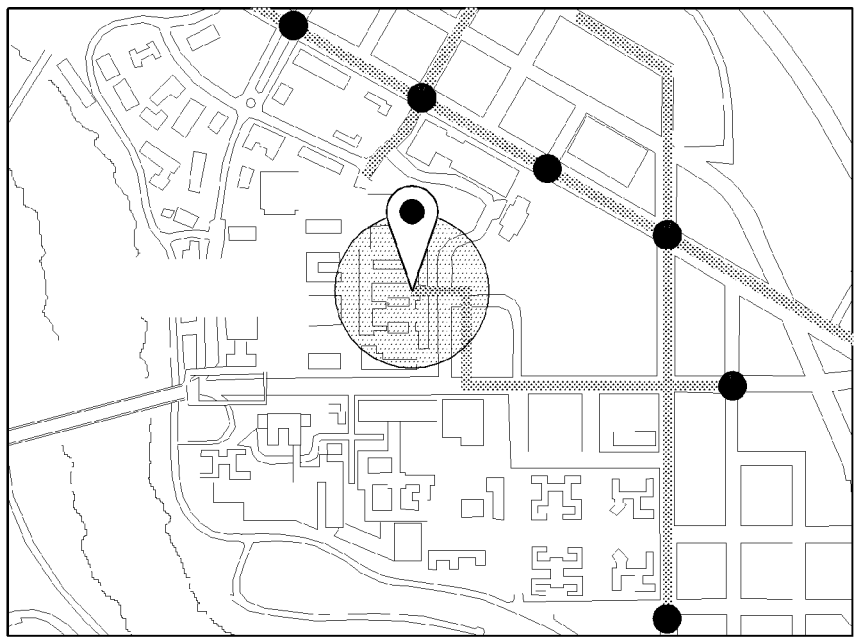

In this case, the artificial intelligence part 130 may acquire the information on the route, along which the user has moved, by interworking with a route finding application as shown in FIG. 13 or by interworking with a navigation application as shown in FIG. 14.

Specifically, when a navigation system has guided the user to a specific route and the user has moved along the specific route, the artificial intelligence part 130 may determine the specific route as the route, along which the user has moved.

In addition, when a navigation system has guided the user to a specific route and the user has moved to a route other than the specific route, the artificial intelligence part 130 may determine the other route as the route, along which the user has moved. In this case, when the same user sitting on the driver's seat again, the artificial intelligence part 130 may guide the user to the other route.

The artificial intelligence part may acquire information on a movement method of the user based on the speed of the user, a movement route, movement of user such as walking or stopping, etc. In this case, the artificial intelligence part may store the movement method along with the route, along which the user has moved.

For example, if the movement route of the user matches the route of the subway line 5 and the user is moving but steps of the user are not detected, the artificial intelligence part may determine that the user is traveling on the subway.

In another example, when the user is moving at a speed of 5 km/h or less and user's steps are detected, the artificial intelligence part may determine that the user is walking.

In another example, when the user is moving at a speed of 80 km/h or more and user's steps are not detected, the artificial intelligence part may determine that the user is traveling using a vehicle.

In another example, when the route of the user matches the route of a bus 100 and user's steps are detected and then are not detected from a bus stop of the bus 100, the artificial intelligence part may determine that the user is traveling on the bus.

Step S1220 of acquiring the information on the movement route to be used by the user based on the past movement route of the user and the current movement of the user will be described.

The artificial intelligence part 130 may acquire the information on the movement route to be used by the user based on the past movement route of the user and the current movement of the user.

For example, when the user has moved along a first route and a second route in the past and the user is currently moving along the first route, the artificial intelligence part may determine that the user will use the first route and then use the second route.

In addition, the artificial intelligence part 130 may acquire information on the current movement method of the user based on the speed of the user, the movement route and the movement of the user such as walking or stopping. In addition, the artificial intelligence part 130 may acquire the information on the movement route to be used by the user based on the current movement method of the user, the current movement of the user, the past movement route of the user and the movement method of the past movement route of the user.

For example, if the user has traveled on the subway along a first route and a second route in the past, has moved on a vehicle along the first route and a third route and the user is currently traveling on the subway along the first route, the artificial intelligence part may determine that the user will use the second route after using the first route.

In addition, the artificial intelligence part 130 may store information on the departure point and destination of the route, along which the user has moved. In addition, the artificial intelligence part 130 may store information on a time required for the user to move along the route.

In this case, the artificial intelligence part 130 may provide a guide to a new route based on the rote information of the movement route to be used by the user.

The route information may include the traffic condition of the route.

For example, when the user is stuck in a traffic jam due to a car accident occurring on the movement route to be used by the user, the artificial intelligence part 130 may output a guide "A traffic jam has occurred due to a car accident occurring on Road 3, so please use Road 2".

Figure 15:
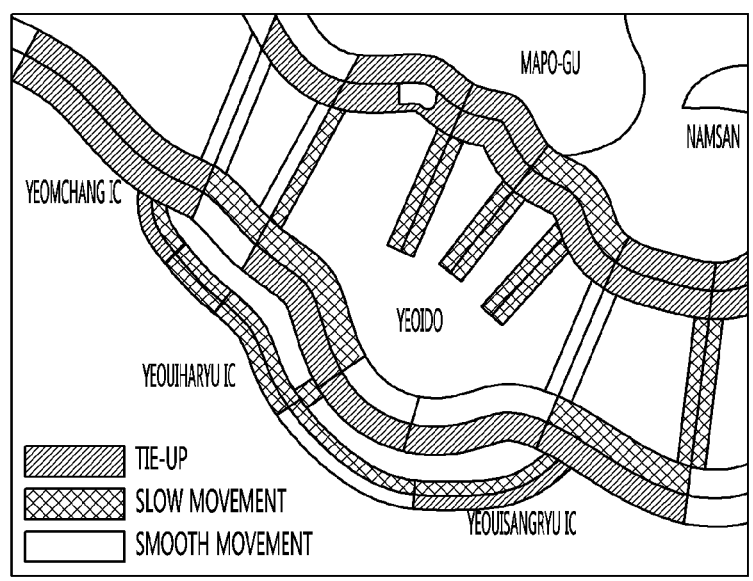

In this case, the artificial intelligence part may receive real-time traffic condition information shown in FIG. 15 from the outside.

Meanwhile, the route information may include a route faster than a route used by the user in the past.

Specifically, if the route used by the user in the past was not the fastest route to a destination, the artificial intelligence part may output the fastest route to the destination.

For example, the route, along which the user has moved in the past, is a first route, a second route and a third route but the fastest route to the destination is the first route, a fourth route and the third route, the artificial intelligence part may output the first route, the fourth route and the third route, which are faster than the route, along which the user has moved in the past.

The artificial intelligence part 130 may provide a guide to a new route based on route information corresponding to the movement route to be used by the user and the movement method.

For example, when the user is current traveling using a vehicle and the route to be used is congested, the artificial intelligence part 130 may provide a guide to a new route, along which the vehicle may travel.

In another example, when the user is currently traveling using a bus and a route, along which the user will move, is congested, the artificial intelligence part 130 may provide a guide to a route to transfer to a subway and get to a destination.

In another example, although the user has traveled in the first compartment of the subway in the past, if getting on the last compartment of the subway is faster in order to transfer the subway, the artificial intelligence part 130 may output a notification indicating that getting on the last compartment of the subway is faster.

In addition, the artificial intelligence part 130 may output information on an estimated time required to move along the movement route to be used by the user based on the route information.

In addition, the artificial intelligence part 130 may output a result of comparing a time required for the user to move along the route in the past with an estimated time required to move along the movement route to be used by the user. For example, the artificial intelligence part 130 may output a message "You will arrive 10 minutes later than yesterday".

Although the movement route to be used by the user is described as being determined based on the route, along which the user moved in the past, in FIGS. 12 to 15, the present disclosure is not limited thereto.

Specifically, the artificial intelligence part 130 may acquire the route pattern of the user based on how often the user uses the route, the number of times that the user uses the route, a time when the user uses the route, etc. with respect to the routes, along which the user traveled in the past.

For example, when the user has traveled along a specific route once or more a week and has used the specific route five times or more, the artificial intelligence part may determine the specific route as the route pattern of the user and store the determined route pattern in the personal database.

In this case, the artificial intelligence part 130 may acquire information on the movement route to be used by the user based on the route pattern of the user and the current movement of the user.

People may maintain the same living habit. For example, people go to work using the same way to work. In this case, in the present disclosure, it is possible to learn a route which is normally used and recommend a faster route in consideration of the traffic condition of the route used by the user or a problem of the route used by the user.

The artificial intelligence part 130 may acquire information on the situation of the user.

Specifically, the artificial intelligence part 130 may acquire information on the situation of the user based on the situation information acquired by the wireless communication unit 110, the sensing unit 140 or the input unit 120, such as the position of the user, the received wireless signal, the speed of the user, the movement route, movement of the user such as walking or stopping, etc.

For example, the artificial intelligence part 130 may determine whether the user rides in a vehicle, a bus or a subway based on the movement route, speed or movement of the user.

In addition, the artificial intelligence part 130 may determine whether the user does grocery shopping or is near a place capable of doing grocery shopping, based on the situation information such as the position of the user, the received wireless signal or the movement of the user.

In addition, the artificial intelligence part 130 may determine whether the user is at home or at work based on the situation information such as the position of the user, the received wireless signal or the movement of the user.

In this case, the artificial intelligence part 130 may output the notification based on the situation of the user.

For example, when the user is riding in a car, the artificial intelligence part 130 may output the notification described with reference to FIGS. 3 to 11.

Figure 12:
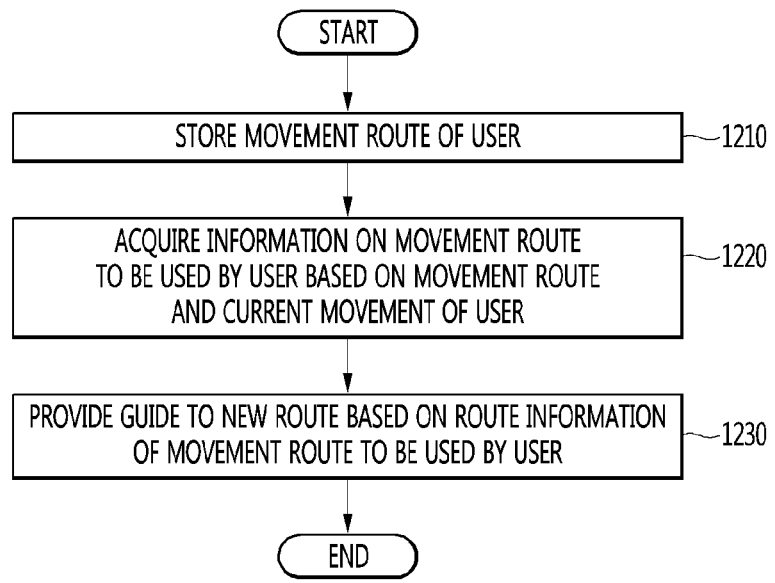

In another example, as described with reference to FIG. 12, the artificial intelligence part 130 may output a notification corresponding to the situation of the user based on the current situation of the user (that is, the movement method of the user).

In another example, if the user does grocery shopping or is near a place capable of doing grocery shopping, the artificial intelligence part 130 may output a notification indicating the consumption state of the user or a notification for purchasing an item.

In another example, when the user is at home, the artificial intelligence part 130 may recommend a life pattern recommended to the user.

Figure 16:
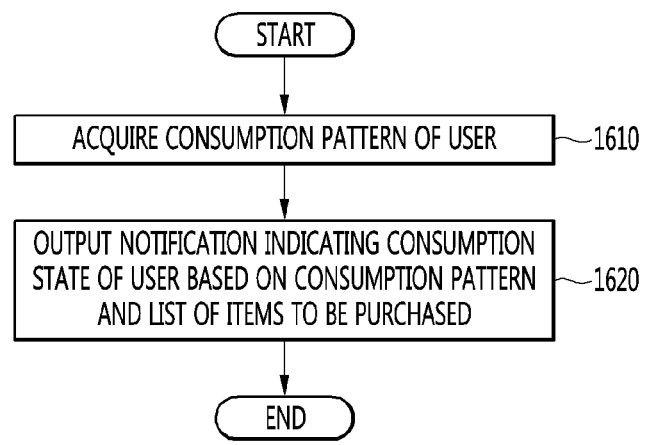
FIGS. 16 to 17 are views illustrating a method of outputting a notification based on a consumption pattern of a user according to an embodiment of the present disclosure.
Figure 17:
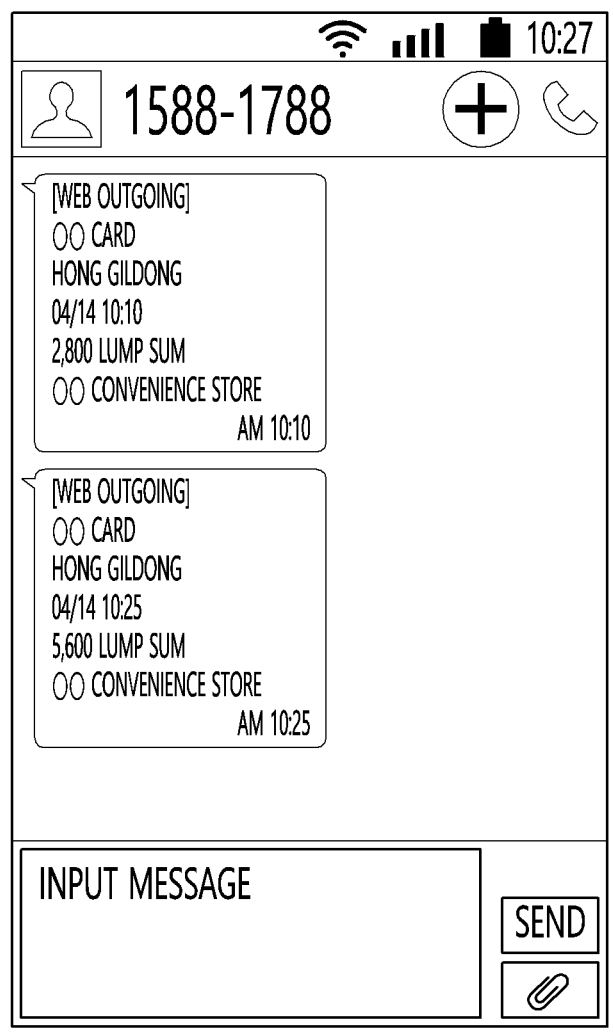

FIGS. 16 to 17 are views illustrating a method of outputting a notification based on a consumption pattern of a user according to an embodiment of the present disclosure.

Referring to FIG. 16, the method of operating the mobile terminal 100 according to the embodiment of the present disclosure may include step S1610 of acquiring the consumption pattern of a user based on the consumption list of the user and step S1620 of outputting a notification indicating the consumption state of the user based on the consumption pattern and the consumption list.

The personal database of the user may include the consumption list of the user.

Specifically, the artificial intelligence part 130 may acquire and store the consumption list of the user in the personal database of the user.

The consumption lit may include at least one of a purchased item, a purchase price, a payment method or a payment time. The payment method may include micro payment, card payment, account transfer, etc.

The artificial intelligence part 130 may acquire the consumption list of the user based on payment information.

For example, the artificial intelligence part 130 may acquire the consumption list of the user using a text message related to micro payment.

In another example, the artificial intelligence part 130 may acquire the consumption list of the user using a payment-related text message received from a card company, as shown in FIG. 17.

In another example, the artificial intelligence part 130 may acquire the consumption list of the user using information included in an account transfer window.

The artificial intelligence part 130 may acquire the consumption pattern of the user based on the consumption list of the user.

Specifically, the artificial intelligence part 130 may acquire the consumption pattern of the user based on at least one of how often a specific consumption appears, the number of times that the specific consumption of the user appears or a time when the specific consumption appears. In addition, the artificial intelligence part 130 may store the acquired consumption pattern in the personal database of the user.

For example, the artificial intelligence part 130 may store consumption of paying for a game item as the consumption pattern of the user, when consumption of paying for the game item appears once or more a week.

In another example, the artificial intelligence part 130 may store consumption of making payment using a micro payment method as the consumption pattern of the user, when consumption of making payment using the micro payment method appears 10 times or more.

In addition, the artificial intelligence part 130 may store the amount of money consumed during a predetermined period as the consumption pattern of the user based on the purchase price. For example, the artificial intelligence part 130 may store information indicating that the user spends an average of 800,000 won per month as the consumption pattern.

The artificial intelligence part 130 may output a notification indicating the consumption state of the user based on the consumption pattern and consumption list of the user.

For example, if the consumption pattern of the user is micro payment and the micro payment is primarily made at the beginning of a month, the artificial intelligence part 130 may output a notification including a message "You tends to make micro payment at the beginning of a month".

In another example, based on a consumption pattern in which the user spends an average of 800,000 won per month and a consumption pattern indicating that 400,000 won is spent up to now on $10^{th}$ day of this month, the artificial intelligence part 130 may output a notification including a message "50% of money spent on the previous month is spent, so you will be in trouble at the end of the month".

The artificial intelligence part 130 may acquire information on an item to be purchased by the user and output a notification indicating the consumption state of the user based on the item to be purchased by the user and the consumption list.

For example, when an image or text related to a lipstick is displayed on the display 151 or a payment site (or a payment window) related to the lipstick is displayed on the display 151, the artificial intelligence part 130 may determine that an item to be purchased by the user is a lipstick. In addition, when a lipstick purchased last week is included in the consumption list, the artificial intelligence part 130 may output a notification "You purchased a lipstick last week".

In the present disclosure, it is possible to induce healthy consumption of the user, by analyzing the consumption pattern of the user and giving a warning.

Figure 18:
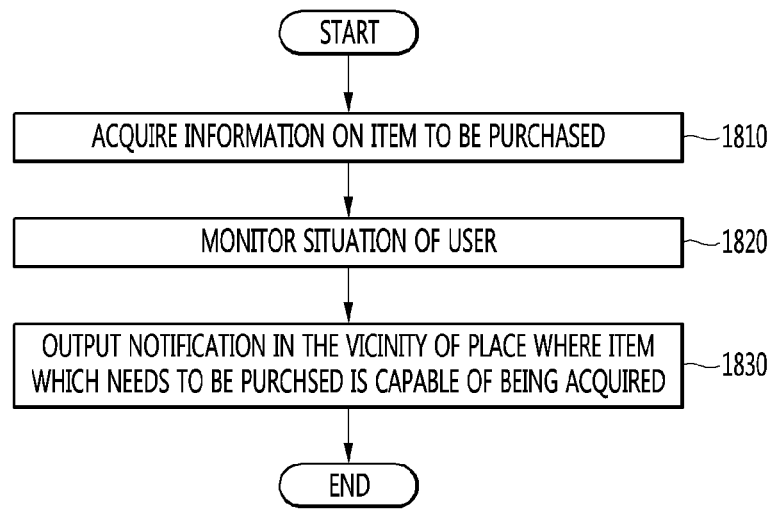
FIG. 18 is a view illustrating a method of providing a guide to an item to be purchased according to an embodiment of the present disclosure.

FIG. 18 is a view illustrating a method of providing a guide to an item to be purchased according to an embodiment of the present disclosure.

The method of operating the mobile terminal 100 according to the embodiment of the present disclosure may include step S1810 of acquiring information on an item which needs to be purchased, step S1820 of acquiring information on the situation of the user, and step S1830 of outputting a notification for purchasing an item in the vicinity of a place where the item which needs to be purchased is capable of being acquired.

Step S1810 of acquiring information on the item which needs to be purchased will now be described.

The personal database may include a list of items.

The list of items may be a list of items purchased by the user or a list of items in the house of the user. The list of items may include a purchased item, a purchase price, a payment method, a purchase time, a distribution period, whether the item is used, a residual ratio of the item, or a purchase frequency.

The list of items may be acquired based on payment information. In addition, the list of items may be acquired based on an image of a payment document such as a receipt.

The artificial intelligence part 130 may acquire information on the item which needs to be purchased based on at least one of the purchase time, purchase frequency or distribution period of an item included in the list of items.

For example, when milk was purchased 15 days ago and the distribution period of milk is 14 days, the artificial intelligence part 130 may determine that milk needs to be purchased.

In another example, when a consumption pattern in which the user purchases milk once every two weeks and the user purchased milk 17 days ago, the artificial intelligence part 130 may determine that milk needs to be purchased.

The artificial intelligence part 130 may acquire information on the situation of the user.

For example, when the user repeatedly walks and stops and is located at a place where a store is located, the artificial intelligence part 130 may acquire information indicating that the user is doing grocery shopping.

In another example, when the user is near a store, the artificial intelligence part 130 may acquire information indicating that the user may purchase an item.

In another example, when the user is near a store but is driving, the artificial intelligence part 130 may acquire information indicating that the user cannot purchase an item.

The artificial intelligence part 130 may output a notification for purchasing an item based on information on the situation of the user.

For example, if the item which needs to be purchased is milk, the artificial intelligence part 130 may receive position information of a store which is selling milk. When the user is near the store, the artificial intelligence part 130 may output a message "Milk was purchased 15 days ago, so milk needs to be purchased".

In another example, the artificial intelligence part 130 may receive the position information of a place where milk is located in the store. In addition, when the user in the store passes the place where milk is located, the artificial intelligence part 130 may output a message "Milk was purchased 15 day ago and the distribution period of milk is 16 days".

In another example, when the user in the store passes a place where toilet paper is located, the artificial intelligence part 130 may receive a wireless signal from the place where toilet paper is located. In addition, among the items in the user's house, there is only little toilet paper. In this case, the artificial intelligence part 130 may output a message "You purchased the toilet paper next to you on $5^{th}$ day of last month and the toilet paper is likely to be be used up after about ten days".

The present disclosure has an advantage of determining the current situation of the user and appropriately providing the information required by the user in the current situation. Specifically, by providing information on a necessary item based on a purchase list and a consumption pattern, it is possible to induce the necessary item to be purchased in an optimal state.

The artificial intelligence part 130 may recommend an item which needs to be purchased based on the situation of the user. For example, when the user is driving, the artificial intelligence part 130 may recommend purchase of an item which needs to be purchased in association with the vehicle.

Figure 19:
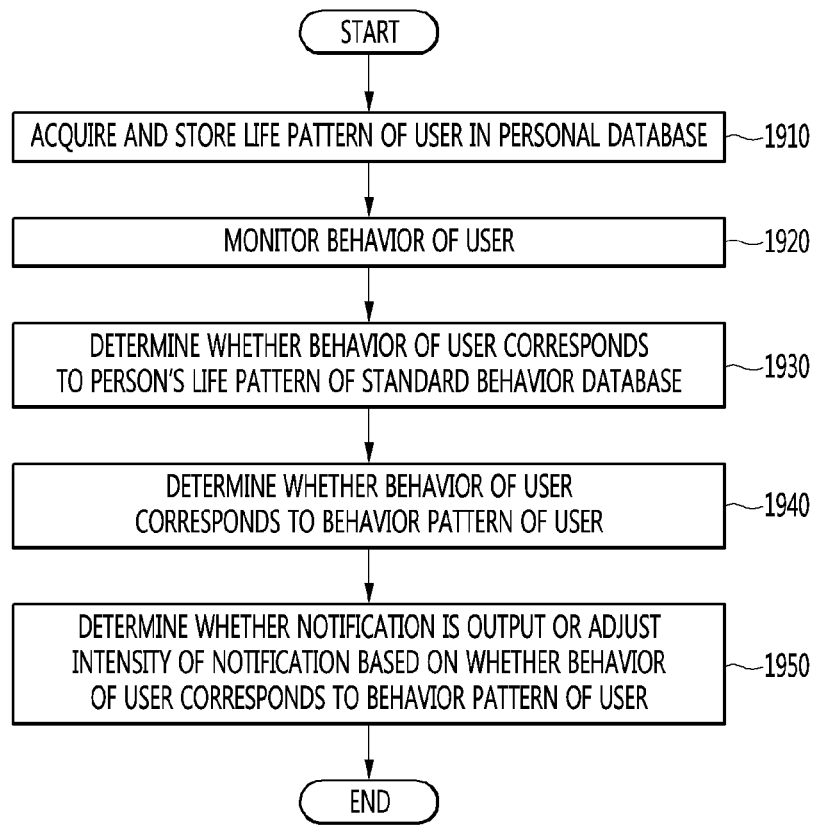
FIG. 19 is a view illustrating a method of outputting a life pattern recommended to a user based on information on a preferable life pattern of a person according to an embodiment of the present disclosure.

FIG. 19 is a view illustrating a method of outputting a life pattern recommended to a user based on information on a preferable life pattern of a person according to an embodiment of the present disclosure.

The method of operating the terminal according to the embodiment of the present disclosure may include step S1910 of acquiring and storing a life pattern of a user in a personal database, step S1930 of acquiring information on the behavior of the user, step S1930 of determining whether the behavior of the user corresponds to the behavior of a person of the standard behavior database, step of S1940 of determining whether the behavior of the user corresponds to the behavior pattern of the user when the behavior of the user corresponds to the behavior of the person of the standard behavior database, and step S1950 of determining whether a notification is output or adjusting the intensity of the notification based on whether the behavior of the user corresponds to the behavior pattern of the user.

The database may include the personal database of the user.

Step S1910 of acquiring and storing the life pattern of the user in the personal database will now be described.

The information on the situation of the user may be stored in the personal database of the user. Specifically, the artificial intelligence part 130 may store the information on the behavior of the user in the personal database of the user.

For example, the artificial intelligence part 130 may store information on a time when the user returns home based on the position information of the mobile terminal 100. In addition, the artificial intelligence part 130 may store information on when use of the mobile terminal 100 is terminated or information on a time when use of the mobile terminal 100 is restarted, based on a call duration of the mobile terminal 100, an application usage time and movement of the mobile terminal 100.

The personal database of the user may include information on the life pattern of the user. The life pattern of the user may be acquired based on a plurality of past behaviors of the user.

Specifically, the artificial intelligence part may acquire the life pattern of the user, based on at least one of how often a specific behavior of the user appears, the number of times that the specific behavior of the user appears or a point in time when the specific pattern appears.

For example, if the mobile terminal 100 is used until late every Thursday, the artificial intelligence part 130 may determine that the user goes to sleep late on Thursday.

In another example, if the user makes a telephone call every Monday morning, the artificial intelligence part 130 may determine that the user makes many telephone calls every Monday morning.

In addition, the artificial intelligence part 130 may acquire a life pattern including the sleep time, wakeup time, sleep time of the user based on a time when the mobile terminal 100 is used or movement of the mobile terminal 100.

The artificial intelligence part 130 may acquire information on the current behavior of the user.

In addition, the artificial intelligence part 130 may determine whether the current behavior of the user corresponds to the life pattern of the person of the standard behavior database.

Information on the life pattern of the person is based on the WHO's recommended guideline and may include information on a recommended sleep time, a recommended bedtime, a recommended wakeup time, etc.

For example, if the user is still using the mobile terminal 100 at 2:00 am and the standard behavior database includes information indicating that the recommended bedtime is 11:00, the artificial intelligence part 130 may determine that the behavior of the user does not conform to the life pattern of the person.

In another example, if the user has used the mobile terminal 100 until 2:00 am and has used the mobile terminal 100 again at 7:00 am, and the standard behavior database includes information indicating that the recommended sleep time is eight hours, the artificial intelligence part 130 may determine that the behavior of the user does not conform to the life pattern of the person of the standard database.

If the behavior of the user does not conform to the life pattern of the person of the standard database, the artificial intelligence part 130 may output a warning notification. In addition, the artificial intelligence part 130 may output the recommended life pattern to the user.

For example, the artificial intelligence part 130 may output a message saying "Why don't you reduce the number of telephone calls a little every Monday morning?".

If the current behavior of the person does not conform to the life pattern of the person stored in the standard behavior database, the artificial intelligence part 130 may determine whether the current behavior of the user is stored in the personal database as the life pattern of the user. In this case, the artificial intelligence part 130 may determine whether the notification is output based on whether the current behavior of the user corresponds to the life pattern of the user.

For example, if the user goes to sleep late only once and is not the normal life pattern of the user, the artificial intelligence part 130 may not output the notification.

In another example, if it is Thursday and the user going to sleep late on Thursday is the life pattern of the user, the artificial intelligence part 130 may output a notification "Your bedtime is usually too late on Thursday. Go to bed earlier".

Based on whether the behavior of the user corresponds to the life pattern of the user, the artificial intelligence part 130 may adjust the intensity of the notification.

For example, if the user does not go to sleep until late and this is not the life pattern of the user, the artificial intelligence part 130 may output the notification with a low intensity.

In another example, if the user does not go to sleep until late and this is the life pattern of the user, the artificial intelligence part 130 may output the notification with a high intensity.

The notification with the low intensity and the notification with the high intensity may be distinguished by the level, the frequency and the like.

Outputting a notification whenever a specific life pattern of a user appears may cause fatigue to the user. Accordingly, the present disclosure has an advantage of outputting a warning only with respect to the bad habits of the user, by extracting the life pattern of the user from the behaviors of the user, determining whether a specific behavior of the user is the life pattern of the user, and outputting a warning.

In addition, the user is preferably warned about a bad behavior even if the bad behavior is not the habit of the user. Accordingly, the present disclosure has an advantage of outputting a warning having a high intensity in case of a behavior originating from the habit of the user and outputting a warning having a low intensity in case of a bad behavior which is not the habit of the user, thereby weakly warning the user about a bad behavior which is not a habit and warning the user about a bad habit.

Although whether the notification is output or the intensity of the notification is described as being determined or adjusted based on whether the behavior of the user corresponds to the behavior pattern of the user in FIG. 19, the present disclosure is not limited thereto.

Specifically, the information on the behavior of the user is stored in the personal database of the user as described above, and the artificial intelligence part may determine whether the notification is output or adjust the intensity of the notification based on whether the situation of the user corresponds to the behavior of the user included in the personal database.

Meanwhile, the controller generally controls the device and may be used interchangeably with a central processing unit, a microprocessor, a processor, etc.

The aforementioned present disclosure can also be embodied as computer readable code stored on a computer readable recording medium. The computer readable recording medium is any data storage device that can store data which can thereafter be read by a computer. Examples of the computer readable recording medium include a hard disk drive (HDD), a solid state drive (SSD), a silicon disk drive (SDD), read-only memory (ROM), random-access memory (RAM), CD-ROM, magnetic tapes, floppy disks, optical data storage devices, etc. The computer may also include the processor 180 of a terminal. It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

The invention claimed is:

1. A terminal comprising:
an output interface configured to output a notification;
a memory configured to store a database;
a controller configured to control output of the notification; and
an artificial intelligence interface configured to acquire information on a situation of a user and output a notification when the situation of the user corresponds to information included in the database,
wherein the database includes at least one of a personal database of the user, a standard behavior database or an accident type database,
wherein the standard behavior database includes information on a behavior of a driver while driving, and
wherein the personal database of the user includes information on a behavior pattern acquired from a past behavior of the user, wherein the artificial intelligence interface is configured to acquire information on a behavior of the user, wherein, when the behavior of the user corresponds to the behavior of the driver included in the standard behavior database, the artificial intelligence interface is configured to determine whether the behavior of the user corresponds to the behavior pattern included in the personal database, wherein, based on the determination, the artificial intelligence interface is further configured to adjust an output intensity of the notification to be output.

2. The terminal of claim 1,
wherein the standard behavior database includes information on a position and information on a behavior of a driver at the position, and
wherein the artificial intelligence interface outputs the notification when the user passes the position and the behavior of the user corresponds to the behavior of the driver at the position.

3. The terminal of claim 1,
wherein the standard behavior database includes information on an incorrect behavior of a driver while driving,
wherein the memory includes information on a correct behavior corresponding to the incorrect behavior, and
wherein the artificial intelligence interface outputs the correct behavior when the behavior of the user corresponds to the incorrect behavior.

4. The terminal of claim 1, wherein the artificial intelligence interface acquires and stores a behavior pattern of a user corresponding to the standard behavior database based on a behavior of the user and the standard behavior database, and outputs the notification when the behavior of the user corresponds to the behavior pattern.

5. The terminal of claim 1,
wherein the accident type database includes information on a position and information on an accident type at the position, and
wherein the artificial intelligence interface outputs a notification corresponding to the accident type at the position when the user passes the position.

6. The terminal of claim 5, wherein the artificial intelligence interface acquires information on a driving state of the user, and outputs a notification corresponding to the accident type based on the driving state of the user and the accident type when the user passes the position.

7. The terminal of claim 1, wherein the artificial intelligence interface acquires a driving habit including at least one of information on a traffic regulation violation of the user or information on route deviation of the user, stores the driving habit and position information corresponding to the driving habit in the personal database, and outputs a notification related to the driving habit at a position where the driving habit appears.

8. The terminal of claim 7, wherein the artificial intelligence interface outputs a notification for preventing the traffic regulation violation when the user reaches a position where the traffic regulation violation appears, based on the information on the traffic regulation violation and position information corresponding to the traffic regulation violation.

9. The terminal of claim 7, wherein the artificial intelligence interface outputs a notification for preventing the route deviation when the user reaches a position where the route deviation appears, based on the information on the route deviation and position information corresponding to the information on the route deviation.

10. The terminal of claim 7,
wherein the artificial intelligence interface acquires information on a movement route to be used by the user based on a past movement route of the user and current movement of the user and provides a guide to a new route based on route information of the movement route to be used by the user, and
wherein the route information includes at least one of a traffic condition of the route or a route faster than a route used by the user in the past.

11. The terminal of claim 1,
wherein the personal database includes a consumption list of the user, and
wherein the artificial intelligence interface acquires a consumption pattern of the user based on the consumption list of the user, and outputs a notification indicating a consumption state of the user based on the consumption pattern and the consumption list.

12. The terminal of claim 1,
wherein the personal database includes a list of items of the user, and
wherein the artificial intelligence interface acquires information on an item, which needs to be purchased, based on at least one of a purchase time, a purchase frequency or a distribution period of an item included in the list of items, and outputs a notification for purchasing the item in the vicinity of a place where the item, which needs to be purchased, is capable of being acquired.

13. The terminal of claim 1,
wherein the standard behavior database includes information on a person's life pattern, and
wherein the artificial intelligence interface acquires information on a life pattern of the user, and outputs a warning notification based on information on the life pattern of the user and information on the person's life pattern.

* * * * *